(12) United States Patent
Alkhatib et al.

(10) Patent No.: US 9,867,697 B2
(45) Date of Patent: Jan. 16, 2018

(54) SELF-ACTUATING SEALING PORTIONS FOR A PARAVALVULAR LEAK PROTECTION

(71) Applicant: St. Jude Medical, Cardiology Division, Inc., St. Paul, MN (US)

(72) Inventors: Yousef F. Alkhatib, Edina, MN (US); Tracee Eidenschink, Wayzata, MN (US); Sounthara Khouengboua, Chaska, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 11 days.

(21) Appl. No.: 14/775,365

(22) PCT Filed: Jul. 2, 2013

(86) PCT No.: PCT/US2013/049065
§ 371 (c)(1),
(2) Date: Sep. 11, 2015

(87) PCT Pub. No.: WO2014/143126
PCT Pub. Date: Sep. 18, 2014

(65) Prior Publication Data
US 2016/0030170 A1 Feb. 4, 2016

Related U.S. Application Data

(63) Continuation-in-part of application No. 13/797,418, filed on Mar. 12, 2013, now Pat. No. 9,398,951.

(51) Int. Cl.
*A61F 2/24* (2006.01)

(52) U.S. Cl.
CPC .............. *A61F 2/2418* (2013.01); *A61F 2/24* (2013.01); *A61F 2210/0014* (2013.01);
(Continued)

(58) Field of Classification Search
None
See application file for complete search history.

(56) References Cited

U.S. PATENT DOCUMENTS

| | | | |
|---|---|---|---|
| 3,657,744 A | 4/1972 | Ersek | |
| 4,275,469 A | 6/1981 | Gabbay | |
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |

(Continued)

FOREIGN PATENT DOCUMENTS

| | | |
|---|---|---|
| DE | 19857887 A1 | 7/2000 |
| DE | 10121210 A1 | 11/2002 |
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| EP | 2537487 A1 | 12/2012 |
| FR | 2847800 A1 | 6/2004 |
| FR | 2850008 A1 | 7/2004 |
| WO | 9117720 A1 | 11/1991 |

(Continued)

OTHER PUBLICATIONS

Buellesfeld et al., Treatment of paravalvular leaks through inverventional techniques; Department of Cardiology, Ben University Hospital 2011.

(Continued)

*Primary Examiner* — David Isabella
*Assistant Examiner* — Dinah Baria
(74) *Attorney, Agent, or Firm* — Lerner, David, Littenberg, Krumholz & Mentlik, LLP

(57) ABSTRACT

A prosthetic heart valve (300) for replacing a native valve includes a collapsible and expandable stent (306) having a proximal end (302) and a distal end (304), and a valve assembly (308) including a plurality of leaflets (310), the valve assembly (308) being disposed within the stent. The heart valve (300) further includes a first plurality of elongated legs (320) coupled to the stent (306) and transitionable from an extended configuration to a relaxed configuration. A first sealing portion (322) connected to the first plurality of legs (320) forms a sealing structure (350) when the legs (320) transition to the relaxed configuration to reduce perivalvular leakage between the implanted valve and surrounding tissue.

10 Claims, 20 Drawing Sheets

(52) U.S. Cl.
CPC ............... *A61F 2230/0065* (2013.01); *A61F 2230/0091* (2013.01); *A61F 2250/0069* (2013.01)

(56) References Cited

U.S. PATENT DOCUMENTS

| | | |
|---|---|---|
| 4,994,077 A | 2/1991 | Dobben |
| 5,411,552 A | 5/1995 | Andersen et al. |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,686,842 B2 * | 3/2010 | Pavcnik ............... A61F 2/07 623/1.13 |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |

(56) References Cited

U.S. PATENT DOCUMENTS

| | | |
|---|---|---|
| 8,974,523 B2 | 3/2015 | Thill et al. |
| 8,974,524 B2 | 3/2015 | Yeung et al. |
| 9,398,951 B2* | 7/2016 | Alkhatib .............. A61F 2/2418 |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0215144 A1 | 9/2008 | Ryan et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0082857 A1 | 3/2009 | Lashinski et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2011/0301702 A1 | 12/2011 | Rust et al. |
| 2012/0035722 A1 | 2/2012 | Tuval |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2013/0310928 A1* | 11/2013 | Morriss .................. A61F 2/2418 |
| | | 623/2.12 |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |
| 2016/0296329 A1* | 10/2016 | Alkhatib .............. A61F 2/2418 |

FOREIGN PATENT DOCUMENTS

| | | | |
|---|---|---|---|
| WO | 9716133 | A1 | 5/1997 |
| WO | 9832412 | A2 | 7/1998 |
| WO | 9913801 | A1 | 3/1999 |
| WO | 0128459 | A1 | 4/2001 |
| WO | 0149213 | A2 | 7/2001 |
| WO | 0154625 | A1 | 8/2001 |
| WO | 0156500 | A2 | 8/2001 |
| WO | 0176510 | A2 | 10/2001 |
| WO | 0236048 | A1 | 5/2002 |
| WO | 0247575 | A2 | 6/2002 |
| WO | 03047468 | A1 | 6/2003 |
| WO | 2006073626 | A2 | 7/2006 |
| WO | 2007071436 | A2 | 6/2007 |
| WO | 2008070797 | A2 | 6/2008 |
| WO | 2010008548 | A2 | 1/2010 |
| WO | 2010008549 | A1 | 1/2010 |
| WO | 2010096176 | A1 | 8/2010 |
| WO | 2010098857 | A1 | 9/2010 |
| WO | 2010127041 | A1 | 11/2010 |
| WO | 2011057087 | A1 | 5/2011 |
| WO | 2012177942 | A2 | 12/2012 |
| WO | 2013028387 | A2 | 2/2013 |
| WO | 2013059743 | A1 | 4/2013 |

OTHER PUBLICATIONS

Catheter-implanted prosthetic heart valves, Knudsen, L.L., et al., The International Journal of Artificial Organs, vol. 16, No. 5 1993, pp. 253-262.

De Cicco, Giuseppe, et al. "Aortic valve periprosthetic leakage: anatomic observations and surgical results." The Annals of thoracic surgery 79.5 (2005): 1480-1485.

Gössl, Mario, and Charanjit S. Rihal. "Percutaneous treatment of aortic and mitral valve paravalvular regurgitation." Current cardiology reports 15.8 (2013): 1-8.

(56) References Cited

OTHER PUBLICATIONS

Heat Advisor, "Heart repairs without surgery, Minimally invasive procedures aim to correct valve leakage", Technology Frontier, Sep. 2004, PubMed ID 15586429.
International Search Report and Written Opinion for Application No. PCT/US2013/078291 dated Apr. 7, 2014.
International Search Report and Written Opinion for Application No. PCT/US2013/49065 dated Oct. 16, 2013.
Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.
Muñoz, Daniel Rodriguez, Carla Lázaro Rivera, and José Luis Zamorano Gómez. "Guidance of treatment of perivalvular prosthetic leaks." Current cardiology reports 16.1 (2014): 1-6.
Quaden et al., "Percutaneous aortic valve replacement: resection before implantation", pp. 836-840, European J. of Cardio-thoracic Surgery, 27 (2005).
Rohde, I., Masch, J.-M., Theisen-Kunde, D., Marczynski-Buhlow, M., Bombien Quaden, R., Lutter, G. and Brinkmann, R. (2015), Resection of Calcified Aortic Heart Leaflets in Vitro by Q-Switched 2?μm Microsecond Laser Radiation. Journal of Cardiac Surgery, 30: 157-162. doi: 10.1111/jocs.12481.
Ruiz, Carlos, Overview of PRE-CE Mark Transcatheter Aortic Valve Technologies, Euro PCR, dated May 25, 2010.
Swiatkiewicz, Iwona, et al. "Percutaneous closure of mitral perivalvular leak." Kardiologia polska 67.7 (2009): 762.
Transcatheter Umbrella Closure of Valvular and Paravalvular Leaks, Hourihan et al., Journal of the American College of Cardiology, vol. 20, No. 6, pp. 1371-1377, (1992).
Transluminal Aortic Valve Placement, Moazami, Nader, et al., ASAIO Journal, 1996; 42:M381-M385.
Transluminal Catheter Implanted Prosthetic Heart Valves, Andersen, Henning Rud, International Journal of Angiology 7:102-106 (1998).
Transluminal implantation of artificial heart valves, Andersen, H. R., et al., European Heart Journal (1992) 13, 704-708.
U.S. Appl. No. 29/375,243, filed Sep. 20, 2010.
U.S. Appl. No. 29/375,260, filed Sep. 20, 2010.

\* cited by examiner

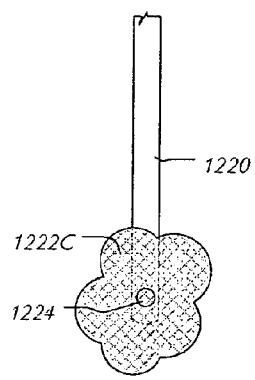 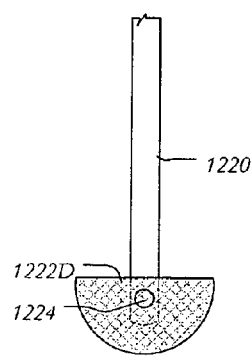
FIG. 12C     FIG. 12D
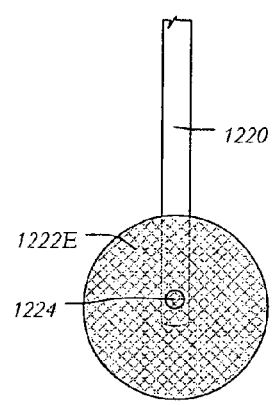 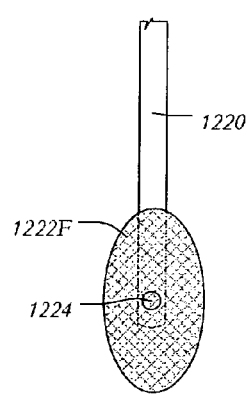
FIG. 12E     FIG. 12F
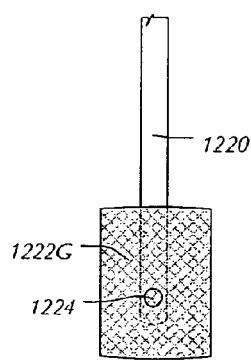 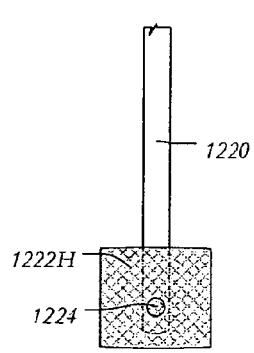
FIG. 12G     FIG. 12H

SELF-ACTUATING SEALING PORTIONS FOR A PARAVALVULAR LEAK PROTECTION

CROSS REFERENCE TO RELATED APPLICATIONS

The present application is a national phase entry under 35 U.S.C. §371 of International Application No. PCT/US2013/049065, filed Jul. 2, 2013, published in English, which claims priority from U.S. patent application Ser. No. 13/797,418 filed Mar. 12, 2013, all of which are hereby incorporated herein by reference.

BACKGROUND OF THE INVENTION

The present disclosure relates in general to heart valve replacement and, in particular, to collapsible prosthetic heart valves. More particularly, the present disclosure relates to devices and methods for positioning and sealing collapsible prosthetic heart valves within a native valve annulus.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

SUMMARY OF THE INVENTION

In some embodiments, a prosthetic heart valve for replacing a native valve includes a collapsible and expandable stent having a proximal end and a distal end, a valve assembly disposed within the stent, the valve assembly including a plurality of leaflets and a plurality of elongated legs, each of the legs having a first end coupled to the stent and a second free end, the elongated legs being configured to transition from an extended configuration to a relaxed configuration. The heart valve may further include a sealing portion connected to the plurality of legs, the sealing portion forming a sealing structure upon the transition of the plurality of legs from the extended configuration to the relaxed configuration.

In some embodiments, a method for implanting a prosthetic heart valve in a native valve annulus may include loading the heart valve in a delivery system, the heart valve including: (a) a collapsible and expandable stent having a proximal end and a distal end, (b) a valve assembly disposed within the stent, the valve assembly including a plurality of leaflets, (c) a plurality of elongated legs configured to transition from an extended configuration to a relaxed configuration, and (d) a sealing portion connected to the plurality of legs, the heart valve being loaded in the delivery system with the plurality of legs in the extended configuration. The method may further include delivering the heart valve to the native valve annulus and deploying the heart valve within the native valve annulus, whereupon the plurality of legs transition from the extended configuration to the relaxed configuration and the sealing portion forms a sealing structure.

BRIEF DESCRIPTION OF THE DRAWINGS

Various embodiments of the present invention will now be described with reference to the appended drawings. It is to be appreciated that these drawings depict only some embodiments of the invention and are therefore not to be considered limiting of its scope.

FIGS. 12C-H are highly schematic longitudinal cross-sectional views of variations of the sealing clusters of FIGS. 12A and 12B.

DETAILED DESCRIPTION

Despite the various improvements that have been made to the collapsible prosthetic heart valve delivery process, conventional devices suffer from some shortcomings. For example, with conventional self expanding valves, clinical success of the valve is dependent on accurate deployment and anchoring. Inaccurate deployment and anchoring of the valve increases risks, such as those associated with valve migration, which may cause severe complications and possibly death due to the obstruction of the left ventricular outflow tract. Inaccurate deployment and anchoring may also result in the leakage of blood between the implanted heart valve and the native valve annulus, commonly referred to as perivalvular leakage (also known as "paravalvular leakage"). In aortic valves, this leakage enables blood to flow from the aorta back into the left ventricle, reducing cardiac efficiency and putting a greater strain on the heart muscle. Additionally, calcification of the aortic valve may affect performance and the interaction between the implanted valve and the calcified tissue is believed to be relevant to leakage, as will be outlined below.

Moreover, anatomical variations from one patient to another may cause a fully deployed heart valve to function improperly, requiring removal of the valve from the patient. Removing a fully deployed heart valve increases the length of the procedure as well as the risk of infection and/or damage to heart tissue. Thus, methods and devices are desirable that would reduce the need to remove a prosthetic heart valve from a patient. Methods and devices are also desirable that would reduce the likelihood of perivalvular leakage due to gaps between the implanted heart valve and patient tissue.

There therefore is a need for further improvements to the devices, systems, and methods for transcatheter delivery and positioning of collapsible prosthetic heart valves. Specifically, there is a need for further improvements to the devices, systems, and methods for accurately implanting a prosthetic heart valve. Among other advantages, the present disclosure may address one or more of these needs.

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve or other medical device into a patient, the terms "trailing" and "leading" are to be taken as relative to the user of the delivery devices. "Trailing" is to be understood as relatively close to the user, and "leading" is to be understood as relatively farther away from the user.

Figure 1:
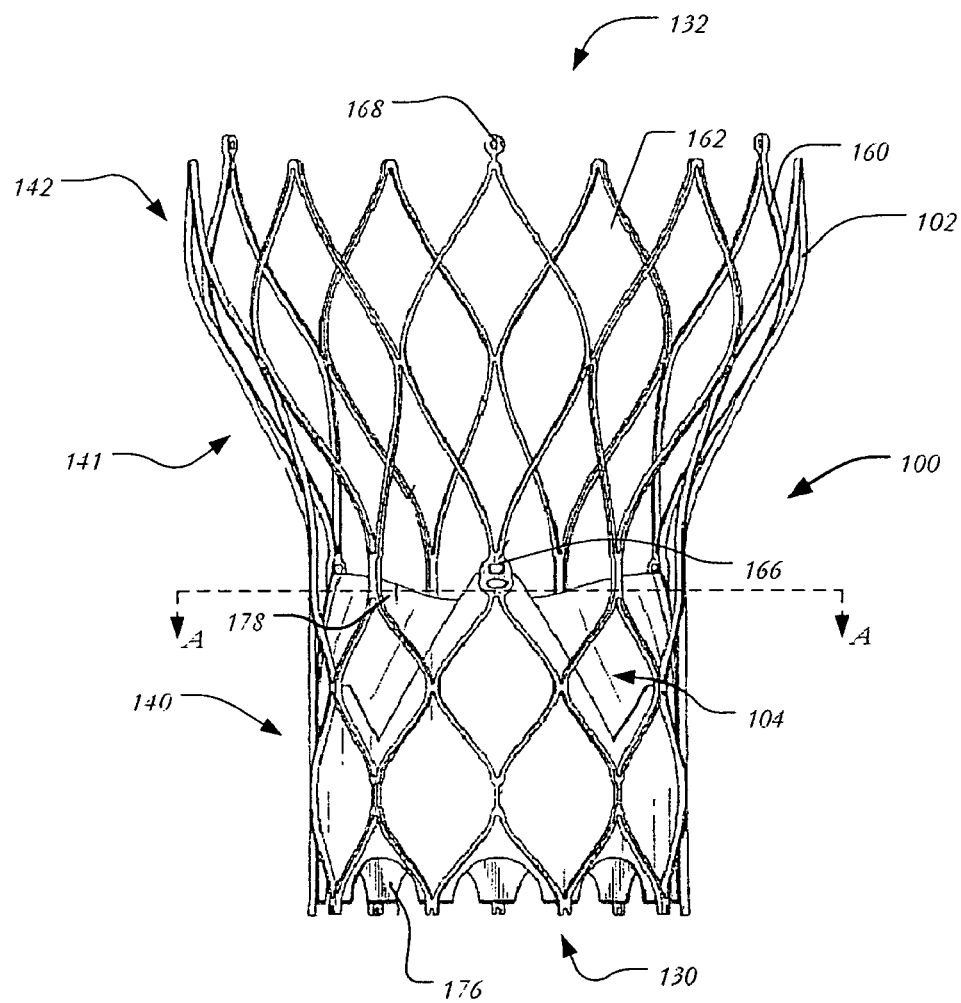
FIG. 1 is a side elevational view of a conventional prosthetic heart valve.

The sealing portions of the present disclosure may be used in connection with collapsible prosthetic heart valves. FIG. 1 shows one such collapsible stent-supported prosthetic heart valve 100 including a stent 102 and a valve assembly 104 as is known in the art. The prosthetic heart valve 100 is designed to replace a native tricuspid valve of a patient, such as a native aortic valve. It should be noted that while the inventions herein are described predominately in connection with their use with a prosthetic aortic valve and a stent having a shape as illustrated in FIG. 1, the valve could be a bicuspid valve, such as the mitral valve, and the stent could have different shapes, such as a flared or conical annulus section, a less-bulbous aortic section, and the like, and a differently shaped transition section.

Prosthetic heart valve 100 will be described in more detail with reference to FIG. 1. Prosthetic heart valve 100 includes expandable stent 102 which may be formed from biocompatible materials that are capable of self-expansion, such as, for example, shape memory alloys, such as the nickel-titanium alloy known as "Nitinol" or other suitable metals or polymers. Stent 102 extends from proximal or annulus end 130 to a distal or aortic end 132, and includes annulus section 140 adjacent proximal end 130, transition section 141 and aortic section 142 adjacent distal end 132. Annulus section 140 has a relatively small cross-section in the expanded condition, while aortic section 142 has a relatively large cross-section in the expanded condition. Preferably, annulus section 140 is in the form of a cylinder having a substantially constant diameter along its length. Transition section 141 may taper outwardly from annulus section 140 to aortic section 142. Each of the sections of stent 102 includes a plurality of struts 160 forming cells 162 connected to one another in one or more annular rows around the stent. For example, as shown in FIG. 1, annulus section 140 may have two annular rows of complete cells 162 and aortic section 142 and transition section 141 may each have one or more annular rows of partial cells 162. Cells 162 in aortic section 142 may be larger than cells 162 in annulus section 140. The larger cells in aortic section 142 better enable prosthetic valve 100 to be positioned in the native valve annulus without the stent structure interfering with blood flow to the coronary arteries.

Stent 102 may include one or more retaining elements 168 at distal end 132 thereof, retaining elements 168 being sized and shaped to cooperate with female retaining structures (not shown) provided on the deployment device. The engagement of retaining elements 168 with the female retaining structures on the deployment device helps maintain prosthetic heart valve 100 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and the heart valve deployed.

Prosthetic heart valve 100 includes valve assembly 104 preferably positioned in annulus section 140 of the stent 102 and secured to the stent. Valve assembly 104 includes cuff 176 and a plurality of leaflets 178 which collectively function as a one-way valve by coapting with one another. As a prosthetic aortic valve, valve 100 has three leaflets 178. However, it will be appreciated that other prosthetic heart valves with which the sealing portions of the present disclosure may be used may have a greater or lesser number of leaflets 178.

Although cuff 176 is shown in FIG. 1 as being disposed on the luminal or inner surface of annulus section 140, it is contemplated that cuff 176 may be disposed on the abluminal or outer surface of annulus section 140 or may cover all or part of either or both of the luminal and abluminal surfaces. Both cuff 176 and leaflets 178 may be wholly or partly formed of any suitable biological material or polymer such as, for example, polytetrafluoroethylene (PTFE).

Leaflets 178 may be attached along their belly portions to cells 162 of stent 102, with the commissure between adjacent leaflets 178 attached to commissure features 166. As can be seen in FIG. 1, each commissure feature 166 may lie at the intersection of four cells 162, two of the cells being adjacent one another in the same annular row, and the other two cells being in different annular rows and lying in end-to-end relationship. Preferably, commissure features 166 are positioned entirely within annulus section 140 or at the juncture of annulus section 140 and transition section 141. Commissure features 166 may include one or more eyelets which facilitate the suturing of the leaflet commissure to stent 102.

Prosthetic heart valve 100 may be used to replace a native aortic valve, a surgical heart valve or a heart valve that has undergone a surgical procedure. Prosthetic heart valve 100 may be delivered to the desired site (e.g., near the native aortic annulus) using any suitable delivery device. During delivery, prosthetic heart valve 100 is disposed inside the delivery device in the collapsed condition. The delivery device may be introduced into a patient using a transfemoral, transapical, transseptal or any other percutaneous approach. Once the delivery device has reached the target site, the user may deploy prosthetic heart valve 100. Upon deployment, prosthetic heart valve 100 expands so that annulus section 140 is in secure engagement within the native aortic annulus. When prosthetic heart valve 100 is properly positioned inside the heart, it works as a one-way valve, allowing blood to flow from the left ventricle of the heart to the aorta, and preventing blood from flowing in the opposite direction.

Problems may be encountered when implanting prosthetic heart valve 100. For example, in certain procedures, collapsible valves may be implanted in a native valve annulus without first resecting the native valve leaflets. The collapsible valves may have critical clinical issues because of the nature of the stenotic leaflets that are left in place. Additionally, patients with uneven calcification, bi-cuspid aortic valve disease, and/or valve insufficiency cannot be treated well, if at all, with the current collapsible valve designs.

The reliance on unevenly calcified leaflets for proper valve placement and seating could lead to several problems, such as perivalvular leakage (PV leak), which can have severe adverse clinical outcomes. To reduce these adverse events, the optimal valve would anchor adequately and seal without the need for excessive radial force that could harm nearby anatomy and physiology.

Figure 2:
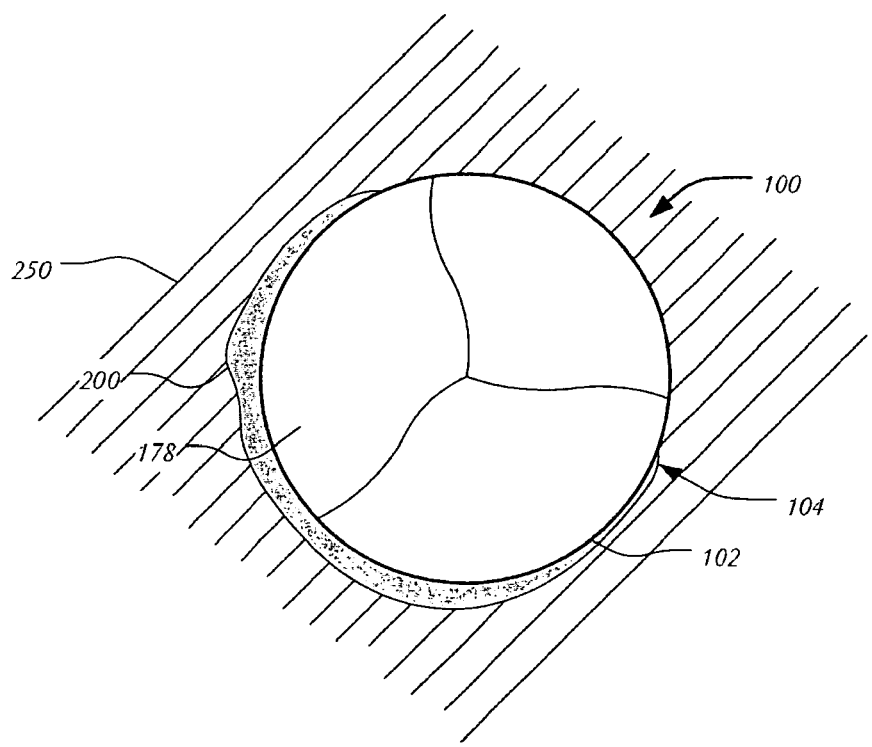
FIG. 2 is a highly schematic cross-sectional view taken along line A-A of FIG. 1 and showing the prosthetic heart valve disposed within a native valve annulus.

FIG. 2 is a highly schematic cross-sectional illustration of prosthetic heart valve 100 disposed within native valve annulus 250. As seen in the figure, valve assembly 104 has a substantially circular cross-section which is disposed within the non-circular native valve annulus 250. At certain locations around the perimeter of heart valve 100, gaps 200 form between heart valve 100 and native valve annulus 250. Blood flowing through these gaps and past valve assembly 104 of prosthetic heart valve 100 can cause regurgitation and other inefficiencies which reduce cardiac performance. Such improper fitment may be due to suboptimal native valve annulus geometry due, for example, to calcification of native valve annulus 250 or to unresected native leaflets.

Figure 3A:
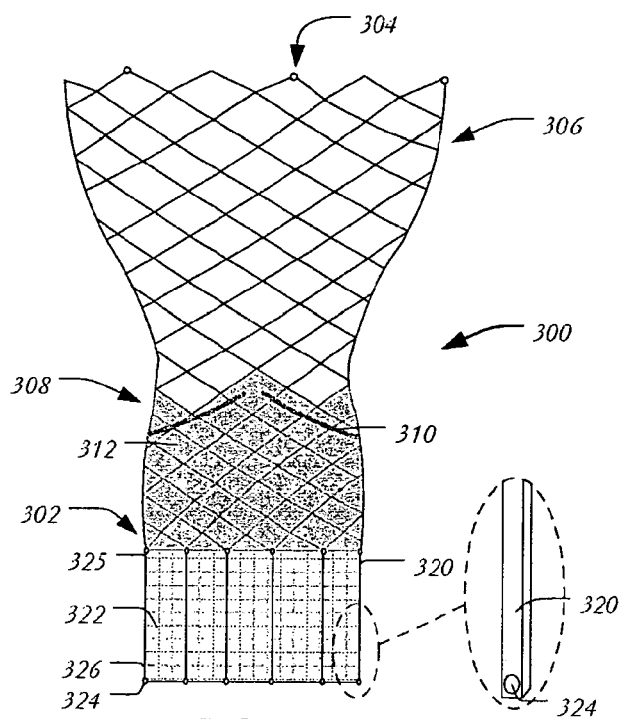
FIGS. 3A and 3B are highly schematic side views of one embodiment of a heart valve having a sealing portion intended to fill irregularities between the heart valve and the native valve annulus.
Figure 3B:
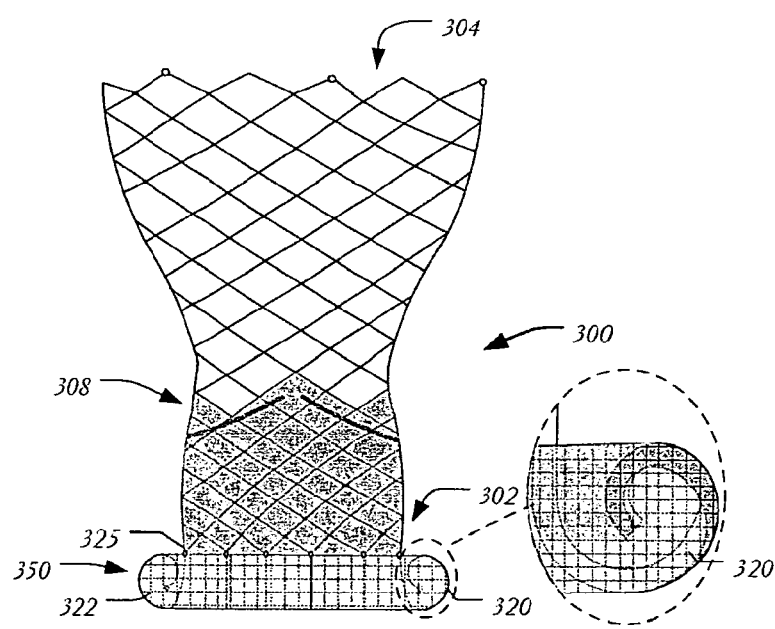

FIGS. 3A and 3B illustrate one embodiment of heart valve 300 intended to fill the irregularities between the heart valve and native valve annulus 250 shown in FIG. 2. Heart valve 300 extends between proximal end 302 and distal end 304, and may generally include stent 306 and valve assembly 308 having a plurality of leaflets 310 and cuff 312. Heart valve 300 may be formed of any of the materials and in any of the configurations described above with reference to FIG. 1.

Additionally, heart valve 300 may include a number of elongated legs 320 and a sealing portion 322 coupled to the elongated legs via eyelets 324 to mitigate perivalvular leakage. Attachment ends 325 of elongated legs 320 may be affixed to stent 306 near the proximal end 302 of heart valve 300, and legs 320 may extend away from the distal end 304 of stent 306 and terminate at free ends 326, which are unattached and free to move. As will be shown in subsequent examples, elongated legs 320 may instead be oriented in the opposition direction, being affixed near the proximal end 302 of heart valve 300 and extending toward the distal end 304 of the heart valve. Attachment ends 325 of elongated legs 320 may be affixed to stent 306 using welding, adhesive, or any other suitable technique known in the art. Additionally, legs 320 may be formed of a shape memory material such as those described above for forming stent 102 of FIG. 1, and may have an extended configuration and a relaxed configuration. In the extended configuration, shown in FIG. 3A, elongated legs 320 may be substantially linear. Moreover, instead of being separately formed and affixed to stent 306 at attachment ends 325, elongated legs 320 may be integrally formed with stent 306, such as by laser cutting both stent 306 and elongated legs 320 from the same tube.

Sealing portion 322 may be attached to legs 320 to form a cylindrical tube around the interior or exterior of the legs. Sealing portion 322 may be attached to legs 320 via sutures, adhesive or any other suitable method. For example, each leg 320 may include eyelets 324 and sealing portion 322 may be attached to eyelets 324 via sutures (not shown). Where eyelets 324 are provided in this or any of the other embodiments described herein, they may be disposed at the free ends of legs 320 as illustrated in FIG. 3A, or anywhere else along the length of the legs. Providing eyelets 324 along the length of legs 320 may better hold sealing portion 322 to the legs as the legs move between their extended and relaxed configurations. Moreover, it will be understood that other features such as indentations or notches may be used to couple two portions of the prosthetic valve using sutures.

Sealing portion 322 may be formed of the same material as cuff 312, including natural materials such as, for example, bovine or porcine pericardium, or synthetic materials such as, for example, ultra-high-molecular-weight polyethylene (UHMWPE), or combinations thereof. In one example, sealing portion 322 may be formed by increasing the length of cuff 312 and extending it over the proximal end 302 and legs 320 of heart valve 300. Alternatively, sealing portion 322 may be formed separately from cuff 312 and attached to eyelets 324 at the proximal end 302 of heart valve 300 to form a seam with cuff 312.

In a variant of the foregoing, sealing portion 322 of heart valve 300 may be formed from a tubular section of braided fabric comprising a plurality of braided strands. The strands forming the braid may have a predetermined relative orientation with respect to one another (e.g., a helical braid). Moreover, sealing portion 322 may comprise a plurality of layers of braided fabric and/or other occluding material such that sealing portion 322 is capable of at least partially inhibiting blood flow therethrough in order to promote the formation of thrombus, endothelialization and epithelialization.

In such variants, sealing portion 322 may be formed of a passive material (e.g., one that does not change shape in response to a stimulus) so that it simply conforms to the shape of legs 320. Alternatively, sealing portion 322 may be formed, for example, of a braided fabric mesh of a shape-memory material, of a super-elastic material, of a biocompatible polymer, or of another material that is capable of being actuated between an extended configuration and a relaxed configuration. Sealing portion 322 may comprise a braided metal fabric that is both resilient and capable of heat treatment to substantially set a desired shape (e.g., the relaxed configuration shown in FIG. 3B). One class of materials which meets these qualifications is shape memory alloys, such as Nitinol. It is also understood that sealing portion 322 may comprise various materials other than Nitinol that have elastic and/or memory properties, such as spring stainless steel, trade named alloys such as Elgiloy®, Hastelloy®, CoCrNi alloys (e.g., trade name Phynox), MP35N®, CoCrMo alloys, mixtures of such alloys or mixtures of metal and polymer fibers. Depending on the individual material selected, the strand diameter, number of strands, and pitch may be altered to achieve the desired properties for sealing portion 322. Thus, sealing portion 322 may alternate between the extended configuration and the relaxed configuration due to the changing shape of legs 320 or alternatively it may itself alternate between the two configurations due to its own shape-memory material properties.

FIG. 3B illustrates the relaxed configuration of heart valve 300. As noted above, legs 320 may have an extended configuration and a relaxed configuration. To effectuate this change in configuration, legs 320 may be curled and subjected to a heat setting process. This process may be accomplished in a series of steps. For example, legs 320 may be formed with a first curl and heat set, and then formed with a second curl and further heat set. The relaxed configuration of legs 320 may therefore include multiple curls due to the curling and heat setting process described above. Legs 320 may be straightened to the extended configuration (shown in FIG. 3A and described above) for cooperation with a delivery system as will be described below with reference to FIGS. 4A-E, and may return to the curled, relaxed configuration after removal from the delivery system. As shown in FIG. 3B, when heart valve 300 is permitted to return to its relaxed configuration, legs 320 may curl up toward distal end 304 and pull sealing portion 322 with them, rolling sealing portion 322 up in the process to form sealing ring 350 at proximal end 302 of heart valve 300. Sealing ring 350 may have a radius larger than that of valve assembly 308, the larger radius of sealing ring 350 being capable of filling any gaps between heart valve 300 and the native valve annulus (not shown). The length of sealing ring 350 may depend on the number of curls of legs 320. For example, sealing ring 350 may have a length that is approximately one-half of the length of legs 320. As shown in FIG. 3B, sealing ring 350 is formed below proximal end 302 and may be suitable for a sub-leaflet application as will be described in greater detail below with reference to FIGS. 8A-8C. Sealing ring 350 may be readily deformable to conform to the shape of the native valve annulus, portions of sealing ring 350 being configured to compress when pressed against the walls of the native valve annulus and other portions of sealing ring 350 being configured to radially expand in gaps, thereby filling the gaps between heart valve 300 and the native valve annulus.

A method of delivering and implanting heart valve 300 will now be described with reference to FIGS. 4A-E. A delivery system 400 may be used to deliver and deploy heart valve 300 in native valve annulus 250, and may generally include sheath 410, core 420, atraumatic tip 430 and hub 440. Sheath 410 may be slidable relative to core 420. Heart valve 300, including stent 306, valve assembly 308, legs 320 and sealing portion 322, may be disposed within sheath 410 about core 420 (FIG. 4A). Hub 440 may be coupled to core 420 and configured to mate with retaining elements 360 of heart valve 300. Elongated legs 320 of heart valve 300 may be disposed in the extended configuration of FIG. 3A, substantially parallel to sheath 410, during delivery. Specifically, though legs 320 are configured to return to their relaxed configuration by curling outwardly, they may be kept substantially linear by being constrained within sheath 410. By doing so, sealing portion 322 and legs 320 may be delivered to the native valve annulus using delivery system 400 without increasing the radius of sheath 410, avoiding the need to increase the crimp profile of the heart valve within delivery system 400. A large delivery system may be incapable of being passed through the patient's vasculature, while a delivery system having a heart valve with a smaller crimp profile may be easier to navigate through a patient's body and may also reduce the operation time. In the example shown in FIGS. 4A-E, delivery system 400 is delivered from the aorta toward the left ventricle as indicated by arrow S1. If heart valve 300 or delivery system 400 includes echogenic materials, such materials may be used to guide delivery system 400 to the appropriate position using the assistance of three-dimensional echocaradiography to visualize heart valve 300 within the patient. Alternative visualization techniques known in the art are also contemplated herein.

Figure 4B:
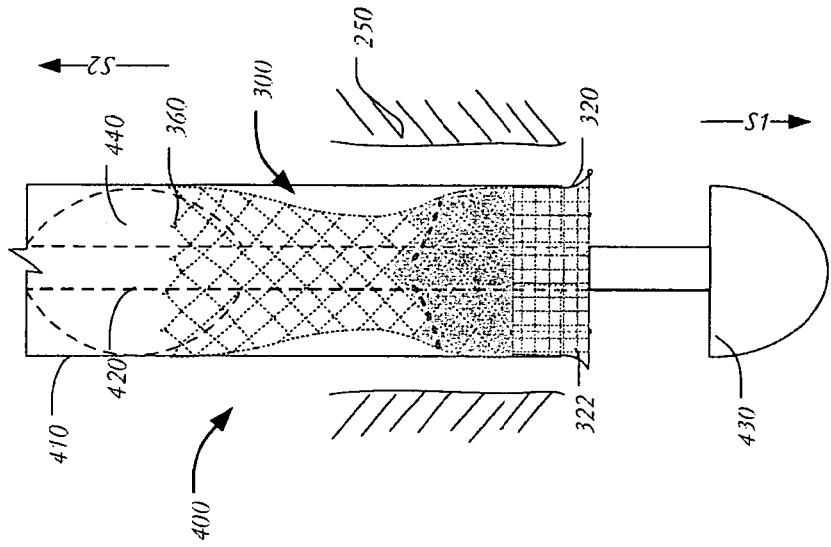
FIGS. 4A-E are highly schematic side views of one method of delivering and deploying the heart valve of FIGS. 3A and 3B within the native valve annulus.
Figure 4A:
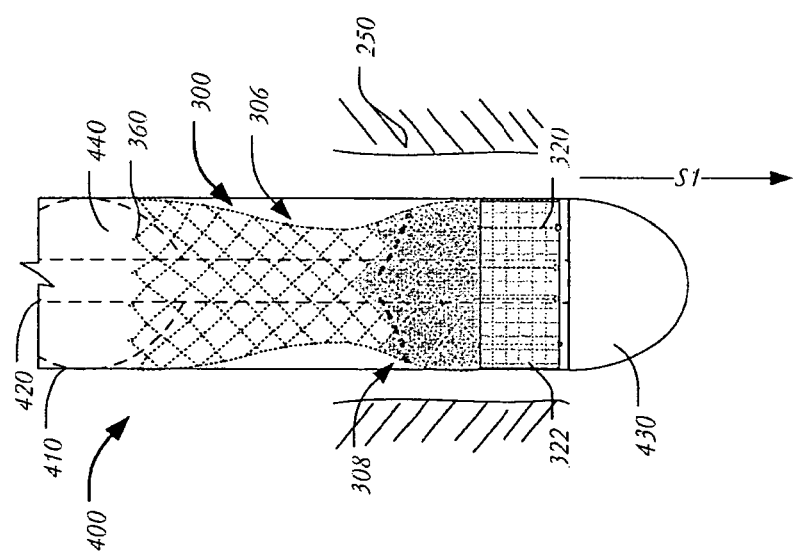
Figure 4C:
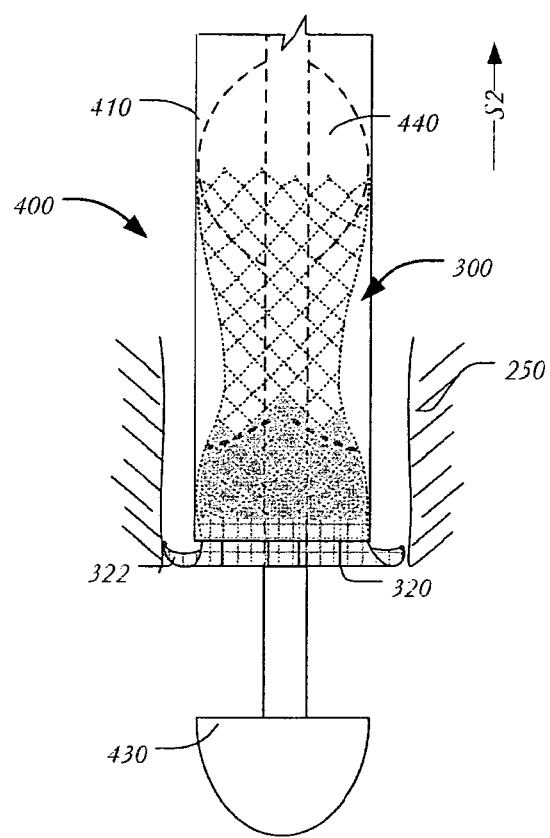
Figure 4E:
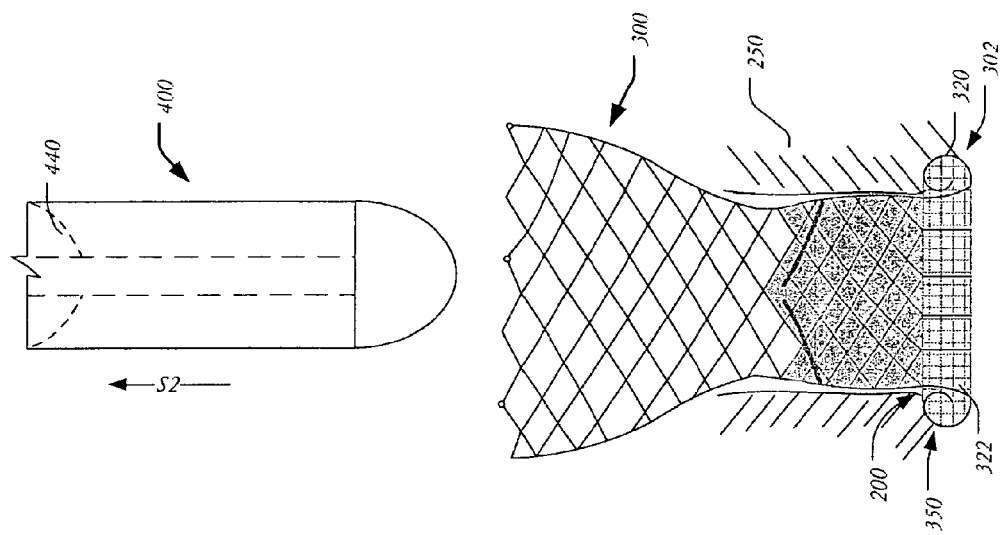
Figure 4D:
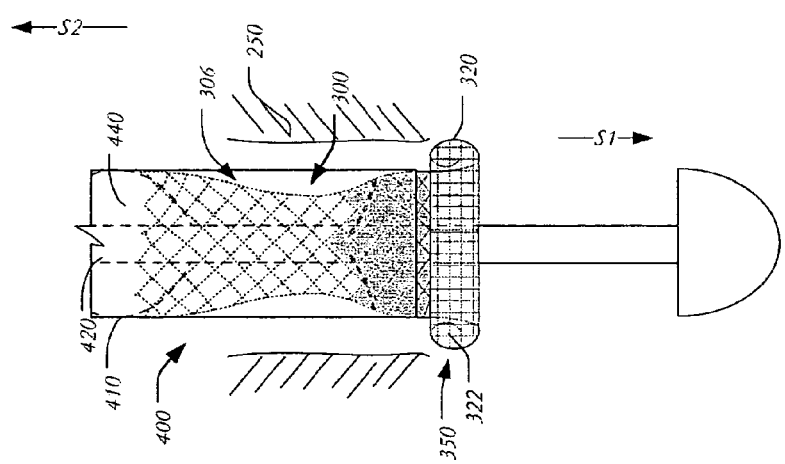

When delivery system 400 has reached the proper location (e.g. atraumatic tip 430 is just past native valve annulus 250), atraumatic tip 430 may be advanced slightly in the direction of arrow S1 toward the left ventricle by pushing core 420 toward atraumatic tip 430 while holding sheath 410 in place which serves to decouple atraumatic tip 430 from sheath 410 (FIG. 4B). Sheath 410 may then be retracted in the direction of arrow S2 toward the aorta. As seen in FIG. 4B, with sheath 410 slightly retracted, legs 320 begin to emerge from the sheath and return to their relaxed configuration by curling outwardly with sealing portion 322, which is attached thereto, curling along with legs 320. As sheath 410 is further retracted in the direction of arrow S2, more of each leg 320 is exposed and curls upon itself (FIG. 4C) until legs 320 fully return to their relaxed configuration (FIG. 4D). Sealing portion 322 attached to curled legs 320 forms sealing ring 350. At this juncture, stent 306 is still disposed within sheath 410 and heart valve 300 has not yet begun to expand. Sheath 410 may be retracted further until heart valve 300 is free to self-expand within native valve annulus 250. While heart valve 300 is partially deployed (e.g., a portion of heart valve 300 is outside sheath 410, but heart valve 300 is not fully detached from delivery system 400), if it appears that heart valve 300 needs to be recaptured and redeployed due to, for example, improper positioning or orientation, sheath 410 may be slid over core 420 in the direction of arrow S1 to recapture heart valve 300 within sheath 410. During recapture, sheath 410 may push against legs 320 to straighten them to the extended configuration shown in FIG. 4A. This process may be repeated until heart valve 300 is properly positioned and deployed within native valve annulus 250. After sheath 410 has been fully retracted to expose heart valve 300, sealing ring 350, being disposed at proximal end 302 of heart valve 300, may occlude gaps 200 between heart valve 300 and native valve annulus 250, thereby reducing or eliminating the amount of blood that passes around heart valve 300 through gaps 200 (FIG. 4E). Retaining elements 360 of heart valve 300 may be decoupled from hub 440 and delivery system 400, including atraumatic tip 430, may then be retracted through heart valve 300 in the direction of arrow S2 and removed from the patient.

Figure 5A:
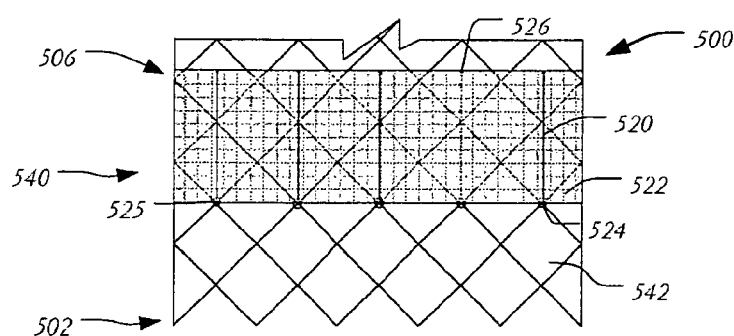
FIGS. 5A and 5B are enlarged highly schematic partial side views of another embodiment of a heart valve having a sealing portion disposed at the annulus section.
Figure 5B:
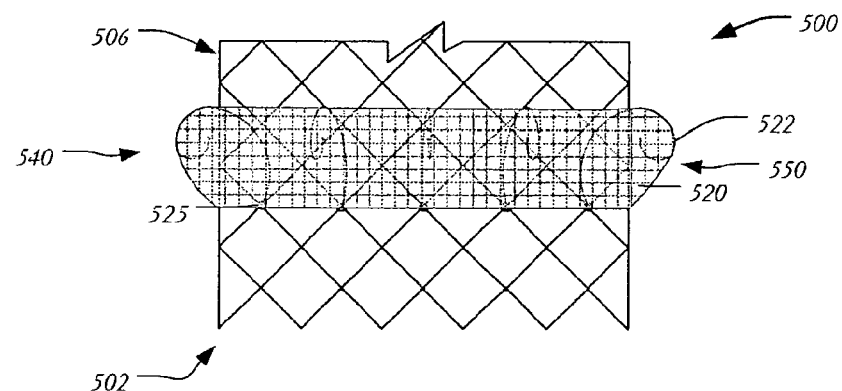

FIGS. 5A and 5B are enlarged schematic partial side views showing heart valve 500 having legs in an extended configuration and in a relaxed configuration, respectively. Heart valve 500 extends between proximal end 502 and a distal end (not shown) and generally includes stent 506 and a valve assembly (not shown for the sake of clarity) having a cuff and leaflets similar to those described above with reference to FIGS. 3A and 3B. Heart valve 500 further includes elongated legs 520 and sealing portion 522 attached to elongated legs 520 at eyelets 524 via sutures. These elements may be formed of any of the materials described above with reference to FIGS. 3A and 3B. Legs 520 may be attached to or formed integrally with stent 506 at attachment ends 525 to couple legs 520 to stent 506. As seen in FIG. 5A, legs 520 may be attached to stent 506 at eyelets 524 near the proximal end 502 of heart valve 500 at the top of the second row of cells 542 of stent 506, and in their extended configuration, may extend substantially linearly toward the distal end of the valve, terminating at free ends 526.

FIG. 5B illustrates the relaxed configuration of legs 520. Legs 520 may be biased so that, when they return to their relaxed configuration, legs 520 curl down toward the proximal end 502 of the valve, as shown in FIG. 5B. Due to the coupling of sealing portion 522 to legs 520, the curling of legs 520 results in a similar curling of sealing portion 522, causing it to roll down in the process to form upper sealing ring 550 within annulus portion 540 of heart valve 500. Upper sealing ring 550 may have a radius larger than that of the valve assembly, and therefore may be capable of filling any gaps between heart valve 500 and the native valve annulus (not shown). As shown in FIG. 5B, sealing ring 550 is spaced from proximal end 502 and may be useful for intra-leaflet applications that are described below with reference to FIG. 8A-C. In at least some examples, sealing ring 550 may be positioned within annulus portion 540 so as to be directly radially outward of the leaflets of heart valve 500 (not shown). Heart valve 500 may be disposed within a delivery system, delivered to the native valve annulus and deployed therein using a delivery system that is the same as or similar to that described in FIGS. 4A-E.

Alternatively, legs 520 may be attached to stent 506 at eyelets 524 and, in the extended condition, may extend substantially linearly toward the proximal end 502 of heart valve 500 so that free ends 526 are closer to proximal end 502 than attachment ends 525. In this alternative example, legs 520 may curl upward toward the distal end to form sealing ring 550. Thus, the location of attachment ends 525 and the direction of the curling of legs 520 may be used to vary the position of sealing ring 550 with respect to heart valve 500.

Figure 5C:
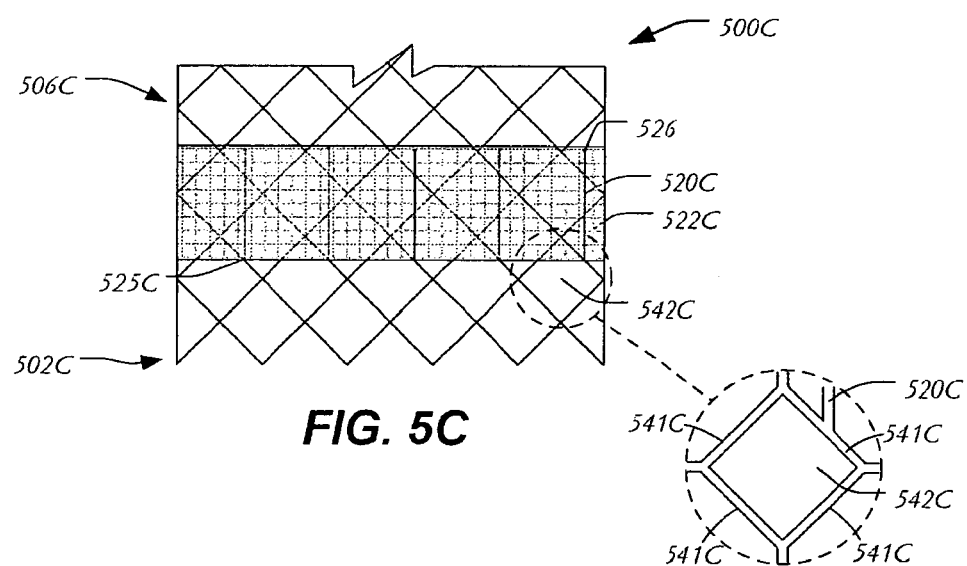
FIG. 5C is an enlarged highly schematic partial side view of another embodiment of a heart valve showing attachment ends of the elongated legs coupled to struts of a stent.

FIG. 5C is an enlarged schematic partial side view showing an alternate extended configuration of the elongated legs. Heart valve 500C extends between proximal end 502C and a distal end (not shown) and generally includes stent 506C and a valve assembly (not shown for the sake of clarity) having a cuff and leaflets similar to those described above with reference to FIGS. 3A and 3B. Heart valve 500C further includes elongated legs 520C and sealing portion 522C attached to elongated legs 520C. These elements may be formed of any of the materials described above with reference to FIGS. 3A and 3B. Legs 520C may be attached to or formed integrally with stent 506C at attachment ends 525C to couple legs 520C to stent 506C. Specifically, legs 520C may be coupled to one or more struts 541C, which form cells 542C or a portion of a cell. Though the previous embodiments have shown attachment ends 525C as being attached to or originating from an intersection of two struts 541C, attachment ends 525C may be coupled to or formed integrally with only one strut 541C. In this example, four struts 541C forming the four sides of cell 542C intersect at four corners of cell 542C, and attachment ends 525C are coupled to a single strut 541C approximately halfway between corners of cell 542C. It will be understood, however, that elongated legs 520C may be coupled to any portion of stent 506C and/or at any location along struts 541C and/or any number of struts. Elongated legs 520C may curl in the same manner described above from a relaxed configuration to form a sealing ring.

Figure 6A:
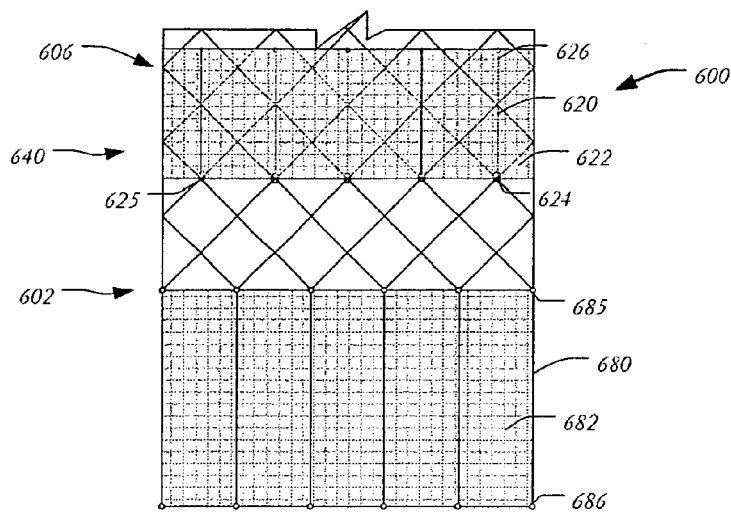
FIGS. 6A and 6B are enlarged highly schematic partial side views of another embodiment of a heart valve having multiple sealing portions.
Figure 6B:
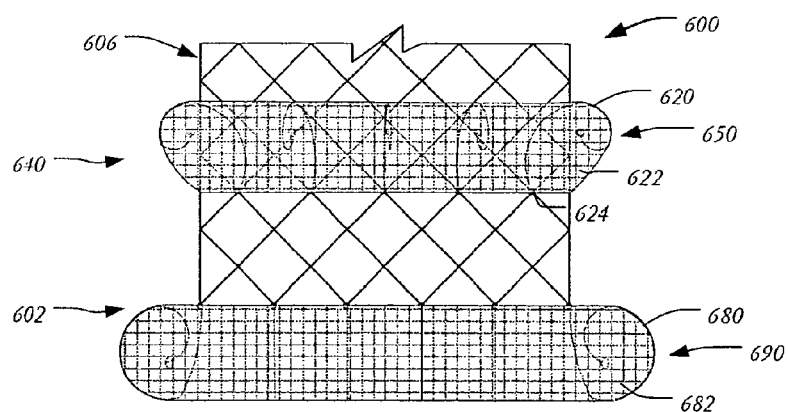

FIGS. 6A and 6B are schematic side views of another embodiment, showing heart valve 600 having legs in an extended configuration and a relaxed configuration, respectively. Heart valve 600 extends between proximal end 602 and a distal end (not shown) and generally includes stent 606 and a valve assembly (not shown for the sake of clarity) having a cuff and leaflets similar to those described above with reference to FIGS. 3A and 3B. Heart valve 600 further includes first elongated legs 620 and first sealing portion 622, which may be attached to first elongated legs 620 at eyelets 624 via sutures. In a configuration similar to that described above with reference to FIGS. 5A and 5B, first legs 620 may be attached to or formed integrally with stent 606 at attachment ends 625 near the proximal end 602 of heart valve 600, and may extend substantially linearly toward the distal end of the valve, terminating at free ends 626. Heart valve 600 further includes second elongated legs 680 attached to stent 606 at second attachment ends 685, which are located at proximal end 602 of the valve, and, in the extended condition, legs 680 extend substantially linearly away from the distal end of the valve to terminate at second free ends 686 beyond proximal end 602 of heart valve 600. A second sealing portion 682, similar to the sealing portion described above in connection with FIGS. 3A and 3B, may be attached to legs 680.

FIG. 6B illustrates the relaxed configuration of the legs of heart valve 600. First legs 620 may be biased so that, when they return to their relaxed configuration, they curl down toward the proximal end 602 of the valve, as shown in FIG. 6B. Due to the coupling of first sealing portion 622 to first legs 620, the curling of first legs 620 results in a similar curling of first sealing portion 622, causing it to roll down in the process to form upper sealing ring 650 within annulus portion 640 of heart valve 600 (e.g. forming a ring at an intra-leaflet position). Likewise, when secondary legs 680 return to their relaxed configuration, they may curl up toward the distal end of heart valve 600, pulling second sealing portion 682 with them to form lower sealing ring 690 (e.g. forming a ring at a sub-leaflet position). When heart valve 600 is implanted using a delivery system similar to that shown in FIGS. 4A-E, lower sealing ring 690 may take shape first as the outer sheath of the delivery system is retracted, followed by upper sealing ring 650. Additional methods may be used to actuate the formation of either of the sealing rings regardless of the delivery approach.

Figure 7A:
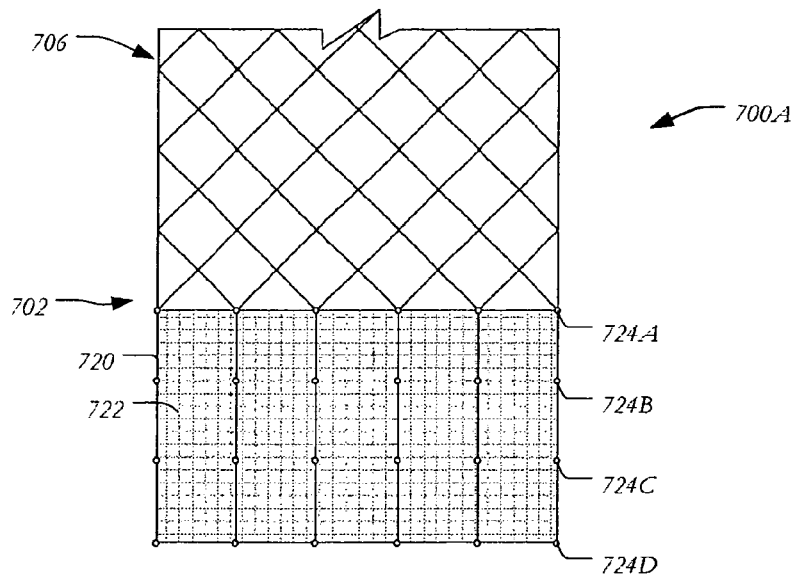
FIG. 7A is an enlarged highly schematic partial side view of another embodiment of a heart valve having elongated legs with multiple eyelets.

FIGS. 7A-D illustrate several additional variants of a heart valve having sealing portions according to the present disclosure. In FIG. 7A, heart valve 700A extends between proximal end 702 and a distal end (not shown) and generally includes stent 706 and a valve assembly (not shown) having a cuff and leaflets. Heart valve 700A further includes elongated legs 720 coupled to stent 706 near proximal end 702, which legs 720, in their extended configuration, may extend substantially linearly away from the distal end of the valve. A sealing portion 722 is coupled to legs 720. In order to provide a more secure attachment of sealing portion 722 to legs 720, each leg 720 may include multiple eyelets 724A-D along its length and sealing portion 722 may be coupled to legs 720 at each of the eyelets. Eyelets 724A-D may be uniformly distributed along the length of each leg 720, as seen in FIG. 7A, resulting in better coupling of sealing portion 722 to legs 720 and a more uniform curling of sealing portion 722 in the formation of a sealing ring.

Figure 7B:
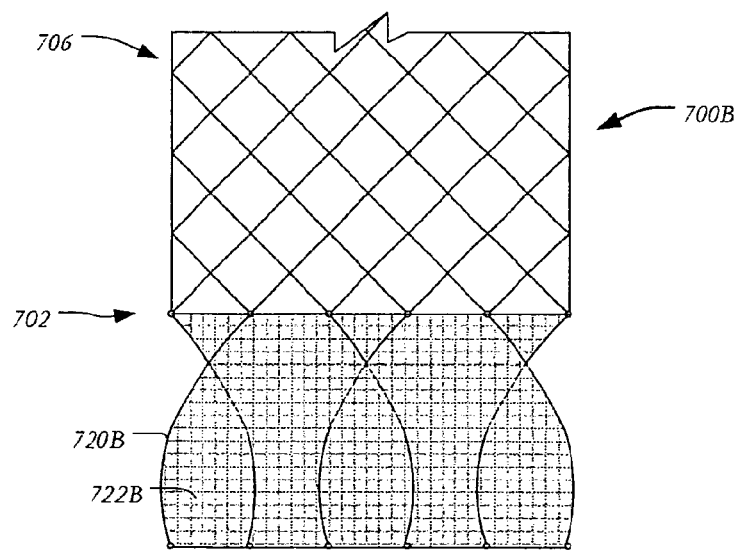
FIG. 7B is an enlarged highly schematic partial side view of another embodiment of a heart valve having wavy legs.

Although the elongated legs in all of the embodiments described above have had a substantially linear configuration in the extended configuration, they may be formed with other configurations. FIG. 7B illustrates a heart valve 700B having nonlinear elongated legs. Heart valve 700B extends between proximal end 702 and a distal end (not shown) and includes stent 706 and a valve assembly having a cuff and leaflets as described above. Heart valve 700B includes elongated legs 720B that are curved or wavy in their extended configuration in contrast to the substantially linear legs of the previous embodiments. Wavy legs 720B may couple to stent 706 at proximal end 702 of heart valve 700B and extend away from the distal end thereof. Legs 720B may be formed to curl in their relaxed configuration in a manner similar to the elongated legs described above. A sealing portion 722B may be attached to legs 720B so as to form a sealing ring in the relaxed configuration of the legs.

Figure 7C:
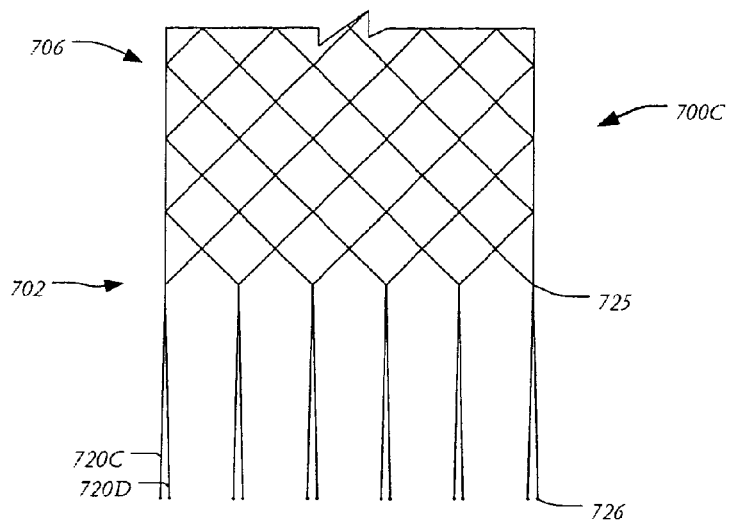
FIGS. 7C and 7D are enlarged highly schematic partial side views of another embodiment of a heart valve having pairs of elongated legs in the extended and relaxed configurations, respectively.
Figure 7D:
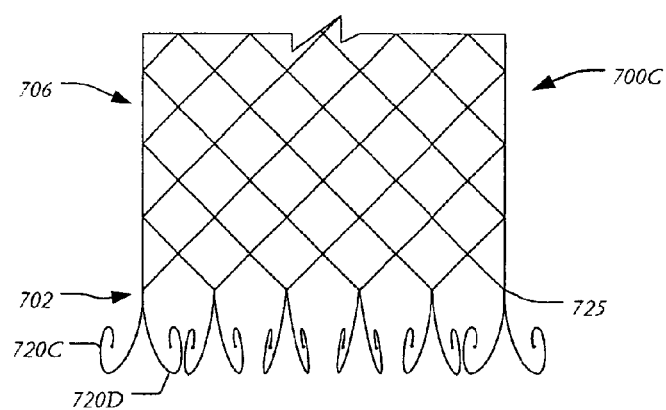

In FIGS. 7C and 7D, another example is shown in which heart valve 700C extends between a proximal end 702 and a distal end (not shown) and includes stent 706 and pairs of elongated legs 720C, 720D. Heart valve 700C further includes a valve assembly having a cuff and leaflets and a sealing portion (none of which are shown for the sake of clarity). In the extended configuration of the legs, shown in FIG. 7C, legs 720C, 720D are formed in pairs that originate at a common attachment end 725 at the apex of a cell at proximal end 702 and extend away from the distal end of heart valve 700C in substantially linear configurations to terminate in independent free ends 726. As shown in their relaxed configuration in FIG. 7D, legs 720C, 720D may curl upward toward the distal end of heart valve 700C along with the attached sealing portion, as previously described, to form a sealing ring. This configuration may provide additional structure for forming and supporting the sealing ring.

As will be appreciated from the embodiments described above, the elongated legs may be attached at the proximal end of a heart valve or anywhere in the annulus portion of the valve. Additionally, in their extended configuration, the elongated legs may extend either toward or away from the distal end of the heart valve, and in their relaxed configuration, may curl in either direction. By varying the points of attachment and the orientation of the elongated legs, sealing rings may be formed at different locations along the valve. In some applications, damaged or calcified native valve leaflets may not be resected prior to implantation of a prosthetic heart valve. The location of the sealing rings may be modified to accommodate the unresected native valve leaflets.

Figures 8A, 8B, 8C:
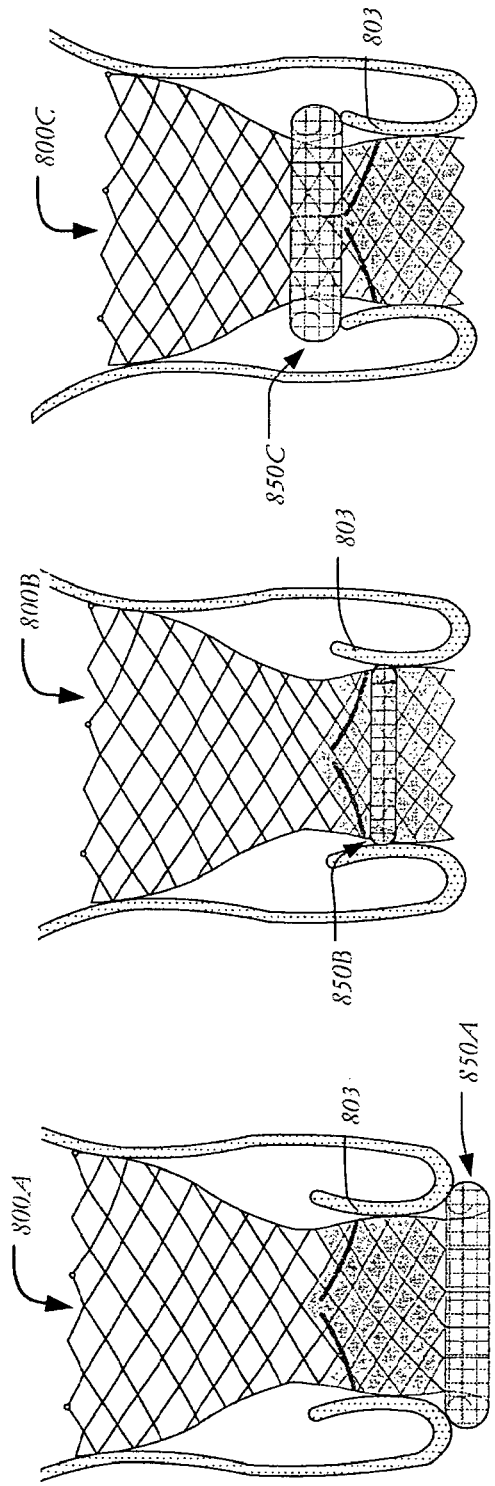
FIGS. 8A-C are highly schematic side views of heart valves having sealing rings disposed at various locations relative to the native leaflets.

FIGS. 8A-8C illustrate heart valves 800A-C disposed within a native valve annulus adjacent unresected native leaflets 803. In FIG. 8A, heart valve 800A includes sealing ring 850A at a proximal end thereof and configured to be disposed below native leaflets 803 (i.e., sub-leaflet location). Sealing ring 850A may be at least partially disposed below native leaflets 803 and may contact the native leaflets to provide a seal between heart valve 800A and native leaflets 803. FIG. 8B illustrates heart valve 800B having a sealing ring 850B spaced distally of the proximal end of the valve and configured to be disposed within native leaflets 803 to provide a seal between heart valve 800B and native leaflets 803 (i.e., intra-leaflet location). FIG. 8C illustrates a heart valve 800C having a sealing ring 850C spaced further distally of the proximal end of the valve and configured to be disposed above the free edges of native leaflets 803 to provide a seal between heart valve 800C and native leaflets 803 (i.e., supra-leaflet location). Thus, sealing rings 850A-C may be disposed at various locations relative to native leaflets 803. It will be appreciated that combinations of any of these sealing rings may be possible. For example, a heart valve may include two sealing rings, a first sealing ring 850A configured to be disposed below native leaflets 803, and a second sealing ring 850C configured to be disposed above the free edges of native leaflets 803. When sealing ring 850A is disposed below the native valve leaflets 803 (FIG. 8A), it may prevent heart valve 800A from migrating into the aorta. When sealing ring 850C is disposed above the native valve leaflets (FIG. 8C), it may prevent heart valve 800C from migrating into the left ventricle. Thus, with this and similar configurations, sealing rings may be used to anchor a heart valve in the native valve annulus, thereby preventing the heart valve from migrating from its intended position.

Figure 9A:
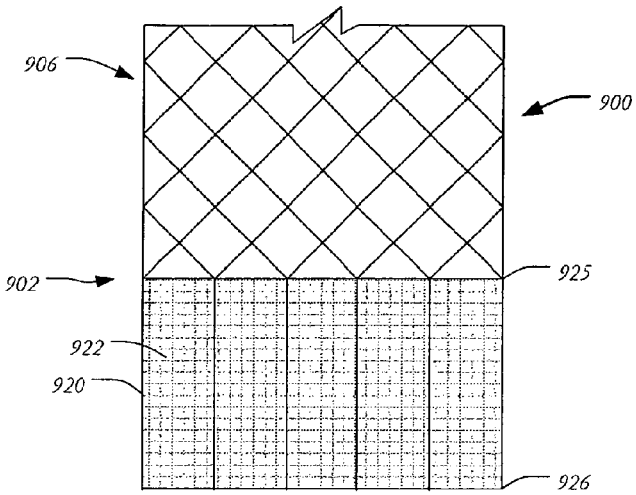
FIGS. 9A and 9B are enlarged highly schematic partial side views of another embodiment of a heart valve having elongated legs in the extended and relaxed configurations, respectively.
Figure 9C:
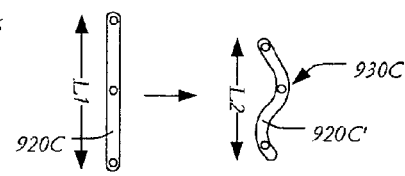
FIGS. 9C and 9D are examples of the shortening of an elongated leg from the extended configuration of FIG. 9A to the relaxed configuration of FIG. 9B.
Figure 9B:
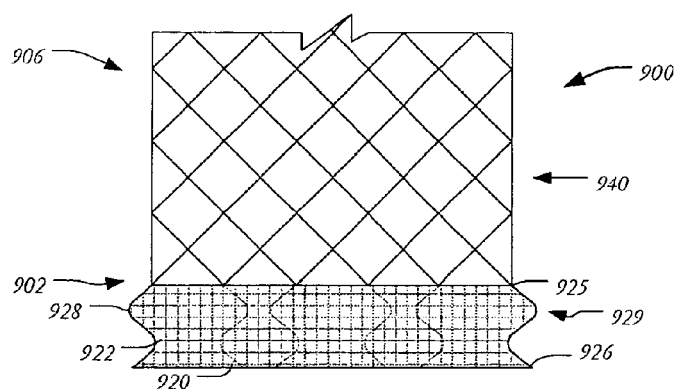

FIGS. 9A and 9B illustrate another embodiment of heart valve 900 having sealing features to mitigate perivalvular leakage. Heart valve 900 of FIG. 9A extends between proximal end 902 and a distal end (not shown) and includes a stent 906, a valve assembly (not shown) including a cuff and leaflets, and elongated legs 920. Legs 920 may be attached to stent 906 at attachment ends 925 near the proximal end 902 of heart valve 900 and, in the extended configuration of the legs shown in FIG. 9A, may extend substantially linearly away from the distal end of the valve, terminating in free ends 926. A sealing portion 922 may be attached to legs 920 in the same manner as the sealing portions described above. When legs 920 of heart valve 900 return to their relaxed configuration, instead of curling over themselves as shown in the previous embodiments, they may axially collapse to form an undulating shape, as seen in FIG. 9B. As a result of this collapse, portions of legs 920 may billow radially out from the profile of the annulus portion 940 of heart valve 900 by an additional distance $d_1$ to form distended portion 928. As shown in FIG. 9B, multiple distended portions 928 may be formed. Each distended portion 928 may extend circumferentially to form a sealing ring 929 or a portion of a sealing ring.

Figure 9D:
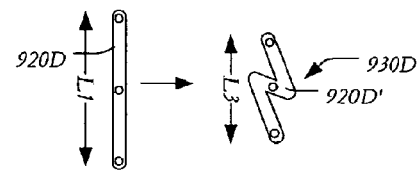

FIG. 9C illustrates a first example of an elongated leg 920C that is capable of collapsing axially to form distended portion 928. In this first example, leg 920C may be substantially linear and have a first length L1 in an extended configuration. Leg 920C may be heat set or otherwise configured to axially collapse to an undulating shape 920C' having a shorter length L2 in the relaxed configuration. When leg 920C assumes undulating shape 920C' it will not only shorten, but will also form convex regions 930C along its length that collectively define distended portions 928 of sealing ring 929. FIG. 9D illustrates another example in which an elongated leg 920D having a length L1 in an extended configuration shortens to an N-shape 920D' having a length L3 in the relaxed configuration. Legs 920D form convex regions 930D along their lengths that collectively define distended portions 928 of heart valve 900. It will be understood that FIGS. 9C and 9D illustrate only two possible examples for forming distended portion 928 and that various techniques and shapes may be used to alternate between a substantially linear elongated leg in the extended configuration and a shortened shape having convex regions in the relaxed configuration.

Figure 10A:
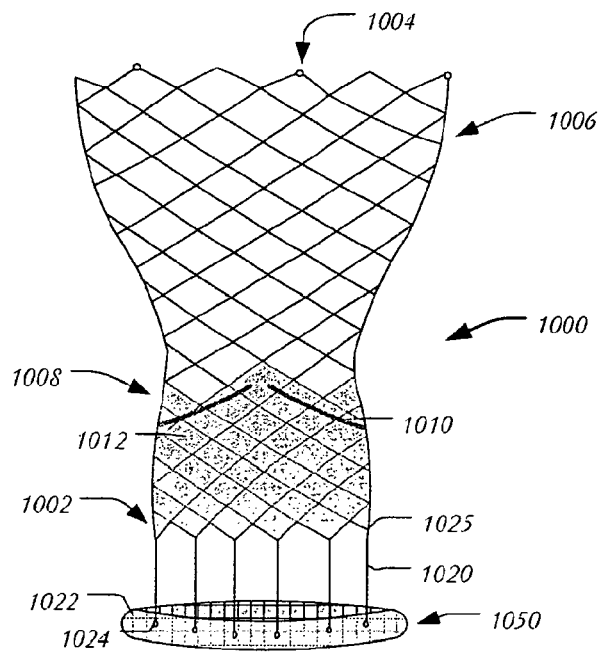
FIGS. 10A and 10B are highly schematic side views of another embodiment of a heart valve having a sealing ring intended to fill irregularities between the heart valve and the native valve annulus.
Figure 10B:
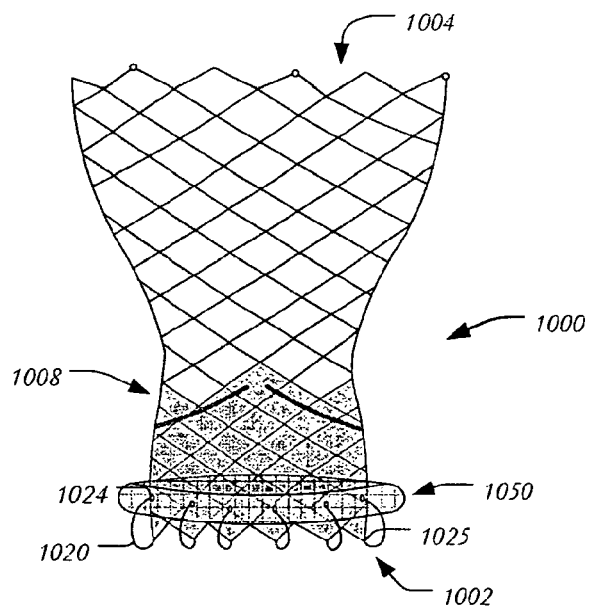

FIGS. 10A and 10B illustrate another embodiment of heart valve 1000. Heart valve 1000 extends between proximal end 1002 and distal end 1004, and may generally include stent 1006 and valve assembly 1008 having a plurality of leaflets 1010 and cuff 1012. Additionally, heart valve 1000 may include a number of elongated legs 1020 and a sealing portion 1022 coupled to the elongated legs via eyelets 1024 to mitigate perivalvular leakage. Legs 1020 may be formed of a shape memory material such as those described above with reference to FIGS. 3A and 3B and may have an extended configuration and a relaxed configuration. Attachment ends 1025 of elongated legs 1020 may be affixed to stent 1006 near proximal end 1002 of heart valve 1000, and legs 1020 may extend away from the distal end 1004 of stent 1006 and terminate at eyelets 1024. In this example, sealing portion 1022 may be in the form of a generally toroidal-shaped sealing ring 1050, regardless of whether legs 1020 are in their extended or relaxed configuration. As used herein, the terms "toroid" and "toroidal" are not limited to a circle revolved about an axis external to the circle which is parallel to the plane of the figure and does not intersect the figure, but also include the revolving of other plane geometrical figures such as, for example, an oval, a triangle, a square and the like. Sealing ring 1050 may be formed of a braided fabric comprising a plurality of braided strands, although it will be understood that any of the other materials described above with reference to FIGS. 3A and 3B may be used as well. In the extended configuration of legs 1020, sealing ring 1050 may be spaced away from proximal end 1002 by the length of the legs.

As noted above, legs 1020 may have an extended configuration and a relaxed configuration. FIG. 10B illustrates the relaxed configuration. When legs 1020 of heart valve 1000 are permitted to return to their relaxed configuration, legs 1020 may curl up toward distal end 1004 and pull sealing ring 1050 over proximal end 1002 of heart valve 1000 so that sealing ring 1050 is at least partially disposed over valve assembly 1008 and/or cuff 1012. Sealing ring 1050 may have a radius larger than that of valve assembly 1008, the larger radius of sealing ring 1050 being capable of filling any gaps between heart valve 1000 and the native valve annulus (not shown). Thus, in this embodiment, sealing ring 1050 is already formed in both the extended and relaxed configurations of legs 1020, but is brought into place for sealing when legs 1020 curl upward in the relaxed configuration.

Figure 10C:
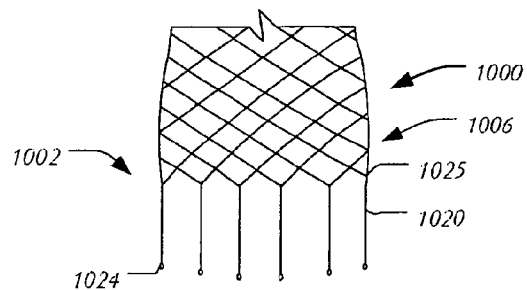
FIGS. 10C-E are highly schematic partial side views of elongated legs in a stretched configuration and two variations of bending the elongated legs.
Figure 10D:
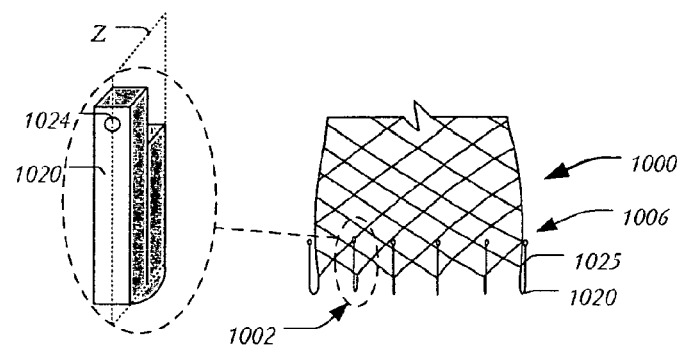
Figure 10E:
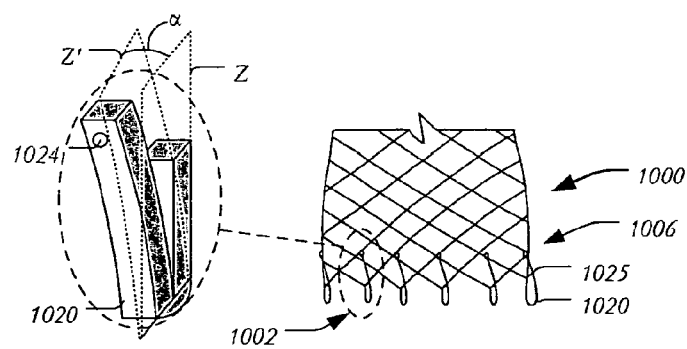

FIGS. 10C-E illustrate the extended configuration of legs 1020 and two examples of the relaxed configuration of legs 1020. As seen in FIG. 10C, in the extended configuration, legs 1020 are coupled to stent 1006 of heart valve 1000 near proximal end 1002 and are substantially linear between eyelets 1024 and attachment ends 1025. In one example shown in FIG. 10D, elongated legs 1020 are configured to curl toward the distal end (not shown) of heart valve 1000, each elongated leg 1020 being bent straight back so as to lie in a single plane Z. Alternatively, as shown in FIG. 10E, each elongated leg 1020 may also be bent with respect to the plane of attachment Z such that it ends in a second plane Z' which forms an angle α with respect to plane of attachment Z. The angle between the two planes may be between about 1 degree and about 60 degrees. By bending leg 1020 in such a manner, leg 1020 may be more conformable, aiding in the transition between the extended and the relaxed configurations.

Figure 10F:
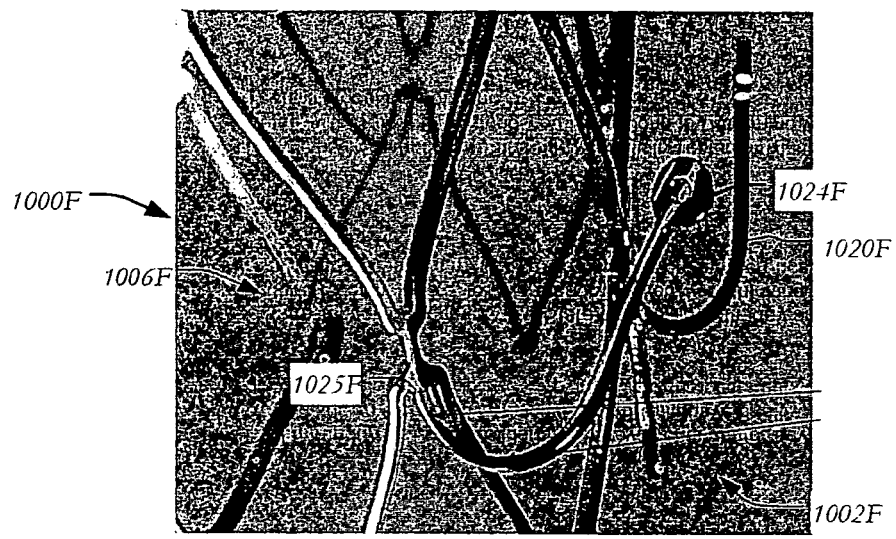
FIG. 10F is an enlarged partial perspective view of the bending of the elongated legs.

FIG. 10F is an enlarged partial perspective view showing the bending of the elongated legs of heart valve 1000F. Heart valve 1000F may extend between proximal end 1002F and a distal end (not shown) and includes stent 1006F and elongated legs 1020F, each having an eyelet 1024F. Elongated legs 1020F may be coupled to stent 1006F at attachment ends 1025F. It may be difficult to bend elongated legs 1020F due to the thickness and width of the legs. Elongated legs 1020F therefore may be twisted along their longitudinal axis in order to more easily bend the legs. In addition to twisting, elongated legs 1020F may be bent as shown above with reference to FIG. 10E. The twisting and bending of elongated legs 1020 may weaken the leg so that a desired stiffness is achieved for proper extension and relaxation of the legs.

Figure 11A:
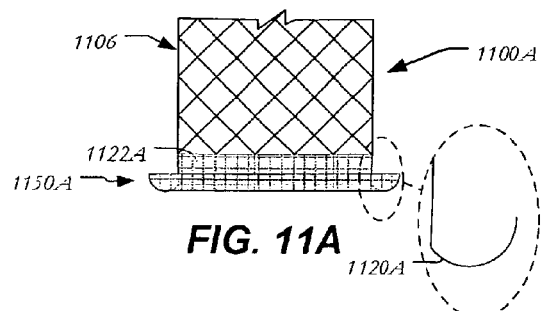
FIGS. 11A-F are highly schematic partial side views of a heart valve showing variations of bending the elongated legs.
Figure 11B:
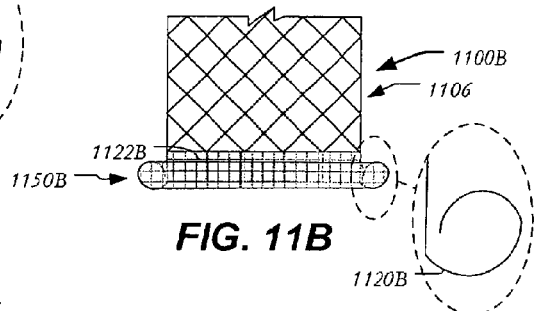
Figure 11C:
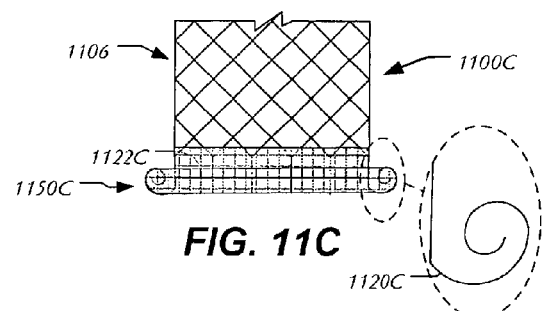
Figure 11D:
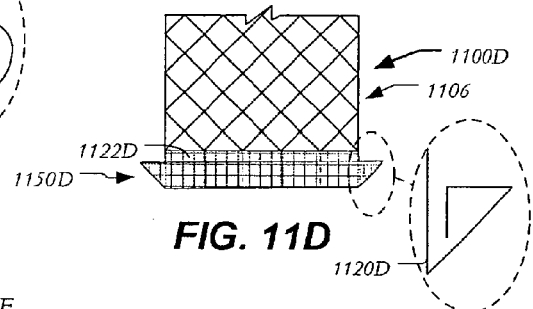

FIGS. 11A-F are highly schematic partial side views of heart valves, showing variations in how the elongated legs are bent in the relaxed configuration. In a first example, heart valve 1100A includes stent 1106 and elongated legs 1120A coupled thereto (FIG. 11A). Elongated legs 1120A of heart valve 1100A bend in the shape of a semicircle, and sealing portion 1122A, which is attached to elongated legs 1120A, curls with elongated legs 1120A to form sealing ring 1150A in the shape of a semicircle revolved about an axis external to the semicircle which is parallel to the plane of the figure and does not intersect the figure. In a second example, heart valve 1100B includes stent 1106 and elongated legs 1120B coupled thereto (FIG. 11B). Elongated legs 1120B of heart valve 1100B bend to form an almost complete circle, and sealing portion 1122B, which is attached to elongated legs 1120B, curls with elongated legs 1120B to form sealing ring 1150B in the shape of an ellipsoid revolved in the manner described above. FIG. 11C illustrates another example in which heart valve 1100C includes stent 1106 and elongated legs 1120C, which bend in multiple curls to stretch sealing portion 1122C to form a spiral-shaped sealing ring 1150C in the shape of a revolved curl. It will be understood from these examples that the elongated legs may include any number of curls or portions of curls.

Figure 11E:
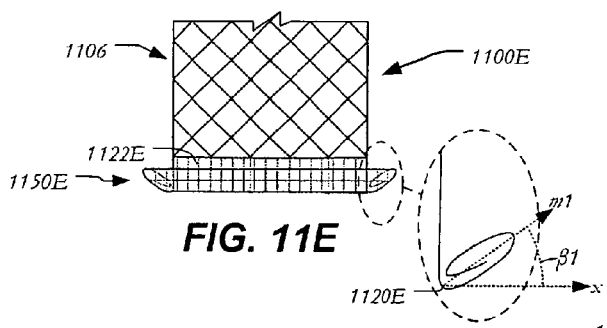
Figure 11F:
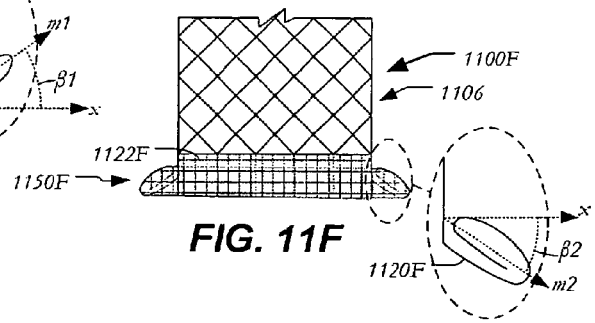

Moreover, the elongated legs may take a number of shapes other than curls. For example, in FIG. 11D, heart valve 1100D includes elongated legs 1120D coupled to stent 1106. Elongated legs 1120D are configured to bend in the shape of a triangle as shown, sealing portion 1122D bending with them to form sealing ring 1150D in the shape of a revolved triangle. FIG. 11E illustrates another example of heart valve 1100E having elongated legs 1120E coupled to stent 1106. Elongated legs 1120E curl in a substantially elliptical shape having a major axis m1 disposed at an upward angle β1 with respect to an axis x extending in the radial direction of heart valve 1100E. In this example, major axis m1 forms an upward angle β1 of about 40 degrees with respect to axis x, causing sealing portion 1122E to form sealing ring 1150E in the shape of a distally-pointing revolved ellipsoid. In an alternative configuration, elongated legs 1120F may be coupled to stent 1106 of heart valve 1100F as shown in FIG. 11F. Elongated legs 1120F curl in a substantially elliptical shape as in FIG. 11E, the ellipse having a major axis m2 disposed at a downward angle β2 with respect to an axis x extending in the radial direction of heart valve 1100F. In this example, major axis m2 forms a downward angle β2 of about 40 degrees with respect to axis x, causing sealing portion 1122F to form sealing ring 1150F in the shape of a proximally-pointing revolved ellipsoid. It will be understood that various modifications may be made to any of these basic shapes of the elongated legs. For example, the foregoing shapes may be inverted when the elongated legs extend toward the distal end of a heart valve (e.g., a triangle that is inverted from that shown in FIG. 11D). Thus, the elongated legs may take any desired shape to form sealing rings of various profiles and radiuses to adequately seal the region between the heart valve and the native valve annulus.

Figure 12A:
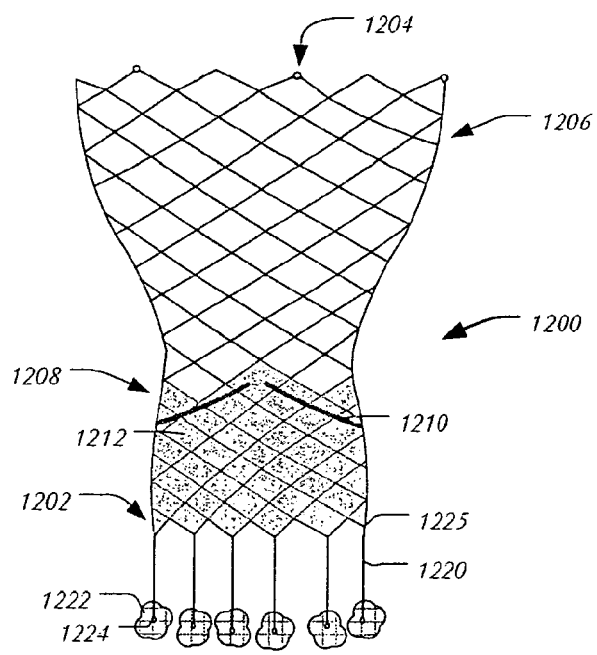
FIGS. 12A and 12B are highly schematic side views of another embodiment of a heart valve having sealing clusters intended to fill irregularities between the heart valve and the native valve annulus.
Figure 12B:
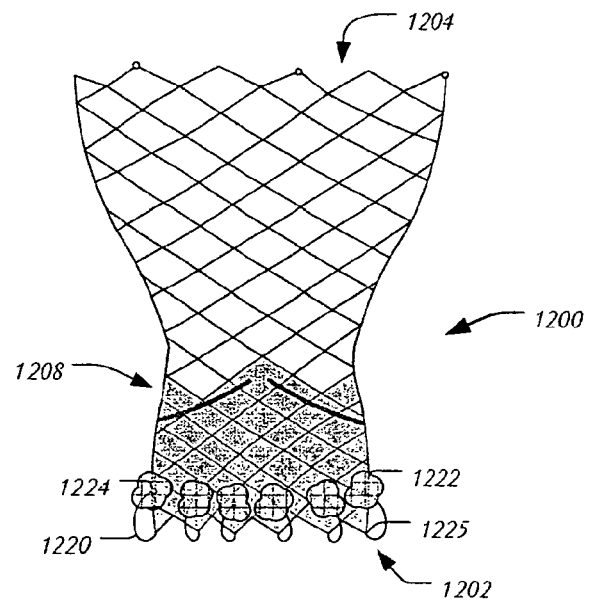

FIGS. 12A and 12B illustrate another embodiment of heart valve 1200. Heart valve 1200 extends between proximal end 1202 and distal end 1204, and may generally include stent 1206 and valve assembly 1208 having a plurality of leaflets 1210 and a cuff 1212. Additionally, heart valve 1200 may include a number of elongated legs 1220 and sealing clusters 1222 coupled to the elongated legs via eyelets 1224 to mitigate perivalvular leakage. Elongated legs 1220 may be formed of a shape memory material such as those described above with reference to FIGS. 3A and 3B and may have an extended configuration and a relaxed configuration. Attachment ends 1225 of elongated legs 1220 may be affixed to stent 1206 near proximal end 1202 of heart valve 1200, and legs 1220 may extend away from the distal end 1204 of stent 1206 and terminate at eyelets 1224 to which sealing clusters 1222 are attached. In this example, sealing clusters 1222 may be formed of a braided fabric formed in a three-dimensional body comprising a plurality of braided strands of nitinol, although it will be understood that any of the other materials described above with reference to FIGS. 3A and 3B may be used as well. As shown in FIG. 12A, in the extended configuration, elongated legs 1220 are substantially linear and sealing clusters 1222 are disposed below valve assembly 1208 so as not to add bulk when collapsed inside a delivery device.

As noted above, elongated legs 1220 may have an extended configuration and a relaxed configuration. FIG. 12B illustrates the relaxed configuration. When legs 1220 are permitted to return to their relaxed configuration, they may curl up toward distal end 1204, pulling sealing clusters 1222 into position between heart valve 1200 and the native valve annulus (not shown). Sealing clusters 1222 may be moved independently of one another to fill any gaps between heart valve 1200 and the native valve annulus.

Additionally, sealing clusters 1222 may take any number of shapes and may be attached to elongated legs 1220 via eyelets 1224 as shown in FIGS. 12C-H. For example, FIG. 12C illustrates a globular sealing cluster 1222C having a flower-shaped longitudinal cross-section. FIG. 12D illustrates sealing cluster 1222D having a hemispherical shape with a semicircular longitudinal cross-section. FIG. 12E illustrates sealing cluster 1222E having a spherical shape with a circular longitudinal cross-section. FIG. 12F illustrates sealing cluster 1222F having an ellipsoid shape with an elliptical longitudinal cross-section. FIG. 12G illustrates sealing cluster 1222G having a cylindrical shape with a rectangular longitudinal cross-section, and FIG. 12H illustrates sealing cluster 1222H having a shorter cylindrical shape with a substantially square longitudinal cross-section. Thus, the shape, size and number of sealing clusters 1222 may be varied as desired. In addition, a combination of sealing clusters 1222 having different shapes and sizes may also be used (e.g., a single heart valve 1200 having both spherical sealing clusters 1222E and cylindrical sealing clusters 1222G). Multiple clusters 1222 may also be coupled to each elongated leg 1220. Additionally, the spacing of the sealing clusters may be varied such that sealing clusters 1222 are spaced away from one another or made to overlap with one another. Moreover, the lengths of legs 1220 may be selected to create a larger sealing zone at various locations with respect to the native valve leaflets. For example, shorter legs 1220 may form sub-leaflet sealing zones while longer legs may form a supra-leaflet sealing zones.

Figure 13:
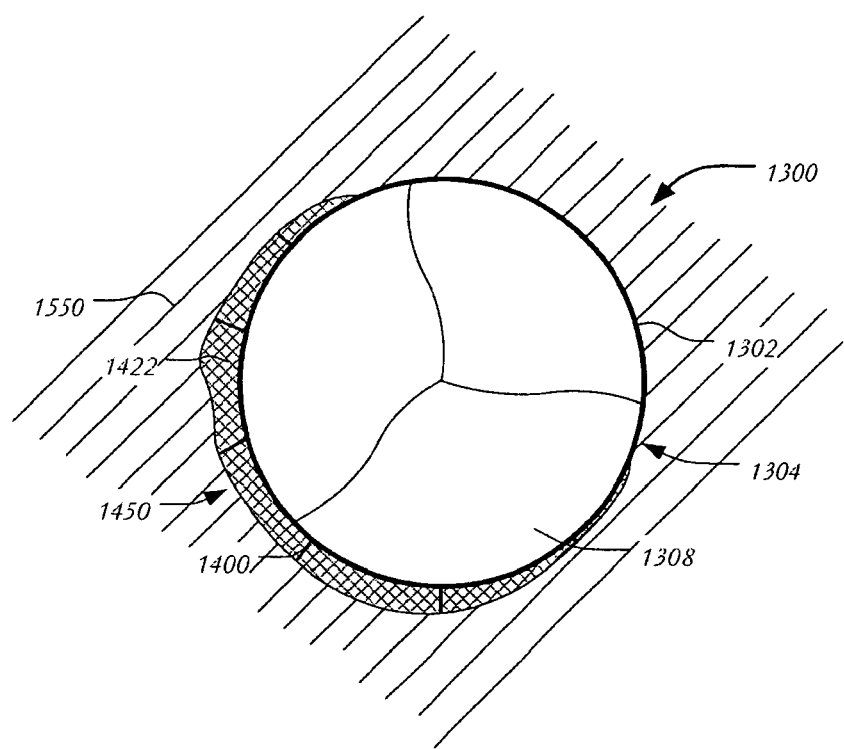
FIG. 13 is a highly schematic cross-sectional view showing a prosthetic heart valve disposed within a native valve annulus and having a sealing ring in its fully expanded state.

FIG. 13 is a highly schematic cross-sectional view showing heart valve 1300 having stent 1302, valve assembly 1304 including a cuff (not shown) and leaflets 1308, and elongated legs 1400 supporting a sealing portion 1422. Legs 1400 have curled up to form sealing ring 1450 and heart valve 1300 has been disposed within native valve annulus 1550. As seen in FIG. 13, sealing ring 1450 has radially expanded to fill gaps 200 shown in FIG. 2, and may be capable of promoting tissue growth between heart valve 1300 and native valve annulus 1550. For example, sealing portion 1422 may be innately capable or promoting tissue growth and/or treated with a biological or chemical agent to promote tissue growth, further enabling sealing ring 1450, when expanded, to seal the heart valve within the native valve annulus. Alternatively, the expanded sealing ring 1450 may be sufficiently dense to adequately seal around heart valve 1300 without the need for major tissue growth. Sealing portion 1422 may also be double-layered and in embodiments having a mesh sealing portion, it may include tighter braiding to more completely occlude the space between heart valve 1300 and native valve annulus 1550. When sealing ring 1450 is functioning properly, heart valve 1300 will be adequately sealed within native valve annulus 1550 so that blood flows through leaflets 1308 of valve assembly 1304, and so that blood flow through any gaps formed between heart valve 1300 and native valve annulus 1550 is limited or reduced.

While the inventions herein have been described for use in connection with heart valve stents having a particular shape, the stent could have different shapes, such as a flared or conical annulus section, a less-bulbous aortic section, and the like, as well as a differently shaped transition section. Moreover, though the elongated legs have been described as having an attachment end and a free end, the elongated legs may be attached to the stent at both ends and exhibit a linear array extended configuration when disposed within a delivery system. The elongated legs may radially expand to form a sealing ring in the relaxed configuration when deployed from the delivery system. Additionally, though the sealing rings have been described in connection with expandable transcatheter aortic valve replacement, they may also be used in connection with other expandable cardiac valves, as well as with surgical valves, sutureless valves and other devices in which it is desirable to create a seal between the periphery of the device and the adjacent body tissue.

The disclosure herein includes a prosthetic heart valve for replacing a native valve comprising a collapsible and expandable stent having a proximal end and a distal end, a valve assembly disposed within the stent, the valve assembly including a plurality of leaflets, a first plurality of elongated legs coupled to the stent transitionable from an extended configuration to a relaxed configuration; and a first sealing portion connected to the first plurality of legs and forming a first sealing structure upon the transition of the first plurality of legs from the extended configuration to the relaxed configuration.

In some examples, each of the plurality of legs may be substantially linear in the extended configuration. Each of the plurality of legs may be curled in the relaxed configuration. The sealing portion may curl to form a sealing ring when the plurality of legs transition from the extended configuration to the relaxed configuration. The sealing ring may be configured and arranged to be disposed below native leaflets of the native valve. The sealing ring may be configured and arranged to be disposed within native leaflets of the native valve. The sealing ring may be configured and arranged to be disposed above native leaflets of the native valve. The plurality of legs may be coupled to the proximal end of the stent and the free ends of the legs extend toward the distal end of the stent in the extended configuration.

In some additional examples, the plurality of legs may be coupled to the proximal end of the stent and the free ends of the legs may extend away from the distal end of the stent in the extended configuration. The sealing portion may include at least one of a metallic mesh or a shape-memory material. The valve assembly may further include a cuff coupled to the stent, the sealing portion and the cuff being made of the same material. The sealing portion may be formed by enlarging the cuff and extending the cuff over the plurality of legs. Each of the plurality of legs may include an eyelet for attaching the sealing portion to the leg. The plurality of legs may be arranged in pairs of legs, each pair of legs being coupled to the stent at a common attachment end. The plurality of legs may billow radially outwardly in the relaxed configuration.

In some examples, the stent may include an annulus portion having a deployed diameter and the sealing portion forms a distended portion having an expanded diameter when the plurality of legs billow radially outwardly in the relaxed configuration, the expanded diameter being larger than the deployed diameter. In some examples, a delivery system for use with the heart valve may include a core and a sheath disposed about the core, the heart valve being disposed about the core and within the sheath.

Moreover, although the inventions herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present inventions as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve for replacing a native valve, comprising:
    a collapsible and expandable stent having a proximal end and a distal end;
    a valve assembly disposed within the stent, the valve assembly including a plurality of leaflets;
    a first plurality of legs coupled to the stent and transitionable from an extended configuration to a relaxed, curled, configuration; and
    a plurality of sealing clusters, each of the plurality of sealing clusters being connected to one of the first plurality of legs and forming a first sealing structure upon the transition of the first plurality of legs from the extended configuration to the relaxed configuration, the plurality of sealing clusters including a metallic mesh.

2. The prosthetic heart valve of claim 1, wherein each of the first plurality of legs is substantially linear in the extended configuration.

3. The prosthetic heart valve of claim 1, wherein the first plurality of legs are coupled to the proximal end of the stent, each of the first plurality of legs having a free end extending away from the distal end of the stent in the extended configuration.

4. The prosthetic heart valve of claim 1, wherein the plurality of sealing clusters includes at least one of a shape-memory material.

5. The prosthetic heart valve of claim 1, wherein each of the first plurality of legs includes an eyelet for attaching one of the plurality of sealing clusters to each of the first plurality of legs.

6. A prosthetic heart valve for replacing a native valve, comprising:
    a collapsible and expandable stent having a proximal end and a distal end;
    a valve assembly disposed within the stent, the valve assembly including a plurality of leaflets;
    a plurality of legs coupled to the stent and transitionable from an extended configuration to a relaxed configuration; and
    a sealing element connected to the plurality of legs, the sealing element being spaced away from the valve assembly in the extended configuration of the plurality of legs and being disposed radially outward of the valve assembly in the relaxed configuration of the plurality of legs, the sealing element including a plurality of sealing clusters, each sealing cluster being attached to one of the plurality of legs, at least some of the plurality of sealing clusters overlapping with one another.

7. The prosthetic heart valve of claim 6, wherein the prosthetic valve is configured and arranged to be disposed in an annulus of the native valve in a deployed condition, and the sealing element is configured to be disposed within leaflets of the native valve in the deployed condition.

8. The prosthetic heart valve of claim 6, wherein the prosthetic valve is configured and arranged to be disposed in an annulus of the native valve in a deployed condition, and the sealing element is configured to be disposed above leaflets of the native valve in the deployed condition.

9. The prosthetic heart valve of claim 6, wherein at least one of the plurality of sealing clusters is spherical.

10. The prosthetic heart valve of claim 6, wherein the sealing cluster on each of the plurality of legs is movable independently from the sealing clusters on the others of the plurality of legs.

* * * * *